(12) United States Patent
Lonky et al.

(10) Patent No.: US 9,186,444 B2
(45) Date of Patent: Nov. 17, 2015

(54) PORTABLE REGULATED PRESSURE DEVICES FOR MEDICAL PROCEDURES

(71) Applicant: MEDITECH DEVELOPMENT INCORPORATED, Yorba Linda, CA (US)

(72) Inventors: Neal M. Lonky, Yorba Linda, CA (US); A. Steve Gurganian, Yorba Linda, CA (US)

(73) Assignee: MEDITECH DEVELOPMENT INCORPORATED, Yorba Linda, CA (US)

( * ) Notice: Subject to any disclaimer, the term of this patent is extended or adjusted under 35 U.S.C. 154(b) by 319 days.

(21) Appl. No.: 13/797,968

(22) Filed: Mar. 12, 2013

(65) Prior Publication Data

US 2014/0276547 A1  Sep. 18, 2014

Related U.S. Application Data

(60) Provisional application No. 61/643,849, filed on May 7, 2012.

(51) Int. Cl.
*A61M 1/00* (2006.01)

(52) U.S. Cl.
CPC ..... *A61M 1/0066* (2013.01); *A61M 2205/3344* (2013.01)

(58) Field of Classification Search
CPC ................. A61M 1/0066; A61M 2205/3344
See application file for complete search history.

(56) References Cited

U.S. PATENT DOCUMENTS

| | | |
|---|---|---|
| 1,294,284 A | 2/1911 | Longeman |
| 1,460,927 A | 2/1922 | Thompson |
| 2,082,782 A | 10/1933 | Allen |
| 3,765,408 A | 10/1973 | Kawai |
| 3,768,477 A | 10/1973 | Anders |
| 4,049,000 A | 9/1977 | Williams |
| 4,314,560 A | 2/1982 | Helfgott |
| 4,957,484 A | 9/1990 | Murtfeldt |
| 4,986,839 A | 1/1991 | Wertz |
| 5,019,086 A | 5/1991 | Neward |
| 5,123,403 A | 6/1992 | Lavyne |
| 5,124,364 A | 6/1992 | Wolff |
| 5,149,331 A | 9/1992 | Ferdman |
| 5,186,711 A | 2/1993 | Epstein |
| 5,196,003 A | 3/1993 | Bilweis |
| 5,224,947 A | 7/1993 | Cooper |
| 5,250,075 A | 10/1993 | Badie |
| 5,259,836 A | 11/1993 | Thurmond |
| 5,281,229 A | 1/1994 | Neward |
| 5,354,268 A * | 10/1994 | Peterson et al. ................. 604/35 |

(Continued)

OTHER PUBLICATIONS

Abboud, "Integration of Reflex Responses in the Control of Blood Pressure and Vascular Resistance", Am. J. Cardiol. 44:904-911 (1979).

(Continued)

*Primary Examiner* — Aarti B Berdichevsky
(74) *Attorney, Agent, or Firm* — Sci-Law Strategies PC

(57) ABSTRACT

In various embodiments of the invention, a vacuum pump can be used as a stand alone unit to create, monitor and control a vacuum in a variety of surgical procedures. The vacuum pump can be controlled by a processor and automatically increases or decreases the vacuum based on monitoring of parameters selected from the group consisting of heart-rate of the fetus, heart rate of the mother, heart rate of patient, blood pressure of the fetus, blood pressure of the mother and blood pressure of the patient, position of the wound, position of the fetus, condition of the fetus, condition of the mother, condition of the patient. Visual or audio feedback is used to allow the care giver increased control of the pumping device while carrying out the procedure.

20 Claims, 9 Drawing Sheets

(56) References Cited

U.S. PATENT DOCUMENTS

| | | | |
|---|---|---|---|
| 5,395,379 | A | 3/1995 | Deutchman |
| 5,423,830 | A | 6/1995 | Chneebaum |
| 5,472,426 | A | 12/1995 | Bonati |
| 5,472,438 | A | 12/1995 | Schmit |
| 5,507,752 | A | 4/1996 | Elliott |
| 5,636,643 | A | 6/1997 | Argenta |
| 5,643,183 | A | 7/1997 | Hill |
| 5,645,081 | A | 7/1997 | Argenta |
| 5,685,821 | A * | 11/1997 | Pike ............................. 600/118 |
| 5,693,058 | A | 12/1997 | Cavanagh |
| 5,727,569 | A | 3/1998 | Benetti |
| 5,762,606 | A | 6/1998 | Minnich |
| 5,769,784 | A | 6/1998 | Barnett |
| 5,799,661 | A | 9/1998 | Boyd |
| 5,810,840 | A | 9/1998 | Lindsay |
| 5,836,311 | A | 11/1998 | Borst |
| 5,865,730 | A | 2/1999 | Fox |
| 5,865,827 | A | 2/1999 | Bullister |
| 5,885,271 | A | 3/1999 | Hamilton |
| 5,891,017 | A | 4/1999 | Swindle |
| 5,906,607 | A | 5/1999 | Taylor |
| 5,935,136 | A | 8/1999 | Hulse |
| 6,074,399 | A | 6/2000 | Wallace |
| 6,506,166 | B1 | 1/2003 | Hendler |
| 6,755,780 | B2 | 6/2004 | Borst |
| 8,323,264 | B2 * | 12/2012 | Weston et al. ................. 604/543 |
| 8,366,692 | B2 * | 2/2013 | Weston et al. ................. 604/319 |
| 8,409,214 | B2 * | 4/2013 | Lonky et al. .................. 606/123 |
| 8,852,170 | B2 * | 10/2014 | Weston et al. ................. 604/543 |
| 2011/0015585 | A1 * | 1/2011 | Svedman et al. ............. 604/290 |

OTHER PUBLICATIONS

Argenta, "Vacuum-Assisted Closure: A New Method for Wound Control and Treatment: Clinical Experience", Ann. Plast. Surg. 38:563-577 (1997).

Bale, "Minimally Invasive Head Holder to Improve the Performance of Frameless Stereotactic Surgery", Laryngoscope 107:373-377 (1997).

Chamberlain, "ABC of Labour Care: Operative Delivery", British Med. J 318:1260-1264 (1999).

Chua Patel, "Vacuum-Assisted Wound Closure", Am. J Nursing 100(12):45-48 (2000).

Jukema, "Vacuum Sealing of Osteomyelitis and Infections of the Soft Tissue", Langenbecks Arch. Chir. Suppl. II 114:581-585 (Kongressbericht 1997).

Kim, "Advances in the Treatment of Organic Erectile Dysfunction", Hosp. Pract. 32:101-120 (1997).

Klemm, "Vacuum-Supported Endoscopic Access", End. Surg. 3:58-62 (1995).

Morykwas, "Vacuum-Assisted Closure: A New Method for Wound Control and Treatment: Ani. Stud. and Basic Found.", Ann. Plast. Surg. 38:553-562 (1997).

Muller, "Vacuum-Sealing Technique in Septic Surgery", Langenbecks Arch. Chir. Suppl. Kongressbd 114:537-541 (1997).

Mullner, "The Use of Negative Pressure to Promote the Healing of Tissue Defects: A Clinical Trial . . . ", Br. J. Plastic Surg. 50:194-199 (1997).

Peolosi, "Use of the Soft Silicone Obsteric Vacuum Cup to Facilitate Delivery and Maniupulation of Large Pelvic . . . ", Am. J. Obsterics and Gynecology 148:337-339 (1984).

Sames, "Sealing of Wounds with Vacuum Drainage", Br. Med. J. 2:1223 (197.

Smith, "Vacuum Pack Technique of Temporary Abdominal Closure: A Four-Year Experience", Am .Surg. 63(12):1102-1108 (1977).

Soderdahl, "The Use of an External Vacuum Device to Augment a Penile Prosthesis", Tech. Urol. 3(2):100-102 (1997).

Won, "Stereotactic Biopsy of Ductal Carcinoma In Situ of the Breast Using an 11-Gu Vacuum-Assisted Dev.: Persisitent . . . ", Am J of Roentgenology 173:227-229 (1984).

* cited by examiner

US 9,186,444 B2

PORTABLE REGULATED PRESSURE DEVICES FOR MEDICAL PROCEDURES

PRIORITY CLAIM

This application claims priority to: (1) U.S. Provisional Patent Application Ser. No. 61/633,849, entitled: "PORTABLE REGULATED VACUUM PUMP FOR MEDICAL PROCEDURES", inventors: Neal M. Lonky and A. Steve Gurganian, filed May 7, 2012, which application is herein explicitly incorporated by reference in its entirety.

FIELD OF THE INVENTION

This invention relates to portable devices that deliver positive and/or negative pressures for medical procedures.

BACKGROUND OF THE INVENTION

A grasping cup, obstetric bonnet, or ventouse cap are some of the names given to the devices used in the field of obstetrics. These devices use a suction cup to assist in the vaginal and operative delivery of newborns. Typically, the suction cup is applied to the fetal scalp during the second stage (pushing through the birth canal) of labor. The obstetrician then applies traction to the infant's head via a flexible or rigid shaft with a handle coupled to the suction cup. The traction is applied in an outward fashion while the delivering mother pushes, thereby assisting in the delivery of the newborn. These suction cups are typically made of silicone, rubber, vinyl or other plastic, or combinations of plastic and rubber. Suction is generally applied through suction tubing which is coupled to a nipple on the vacuum cup, the nipple communicating with the interior of the cup. The method by which the suction is produced can vary from large stationary mechanical vacuum/suction devices to hand-held pumps similar to those which are used to bleed brake fluid from brake lines of automobiles. The suction cup has been reported to be safer than forceps and is intended to more gently ease a baby from the womb than forceps.

Suction devices can also be used to manipulate tissue during surgery. For example, U.S. Pat. No. 5,196,003 to Bilweis, which is explicitly incorporated by reference in its entirety, discloses an endoscopic surgical instrument which includes a tube with a suction cup at one end and a bulb at its opposite end. The cup is placed on a target tissue and the bulb is compressed and released in order to apply suction to the tissue. The tissue is released by again compressing the bulb.

SUMMARY OF THE INVENTION

In an embodiment of the present invention, a pump is used to apply a specified positive or negative pressure to a pumping device attached to a body part. The pumping device comprises the suction device (or suction cup), a sensor for monitoring the vacuum applied to the suction device, a pump for increasing the vacuum to the suction device, a tube for applying the vacuum to the suction device and a control circuit for activating the pump. In an embodiment of the present invention, the control circuit is operated by the surgeon holding the suction device. In an embodiment of the present invention, the surgeon controls the vacuum applied while performing the surgical procedure. In an embodiment of the present invention, the suction device can be manipulated and the pumping device can be controlled by a surgeon alone while the surgical procedure is carried out.

BRIEF DESCRIPTION OF THE DRAWINGS

This invention is described with respect to specific embodiments thereof. Additional features can be appreciated from the Figures in which.

DETAILED DESCRIPTION OF THE INVENTION

Definitions

Figure 1:
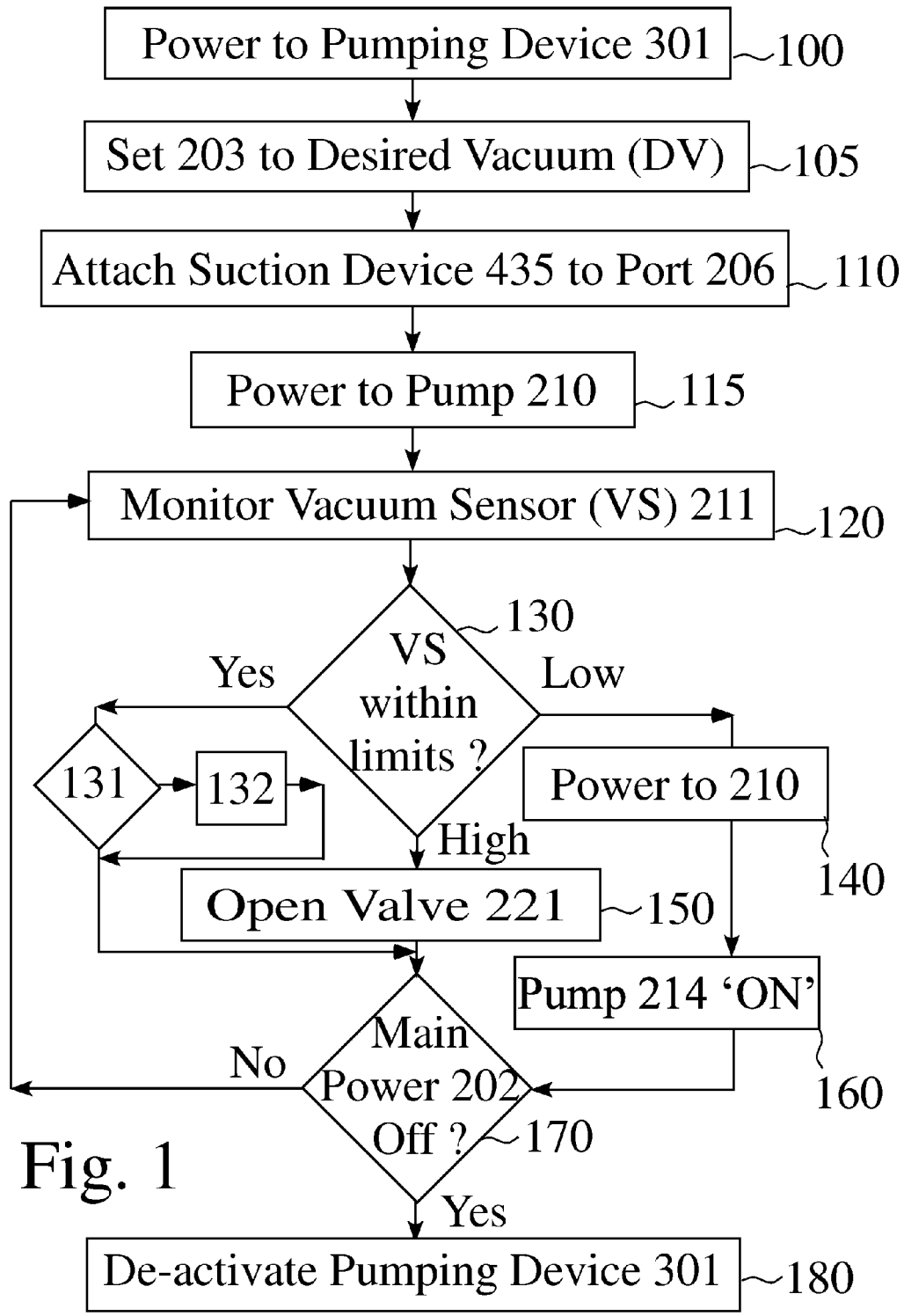
FIG. 1 is a flowchart showing the use of the pumping device 301 in a procedure in accordance with an embodiment of the invention.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

As used herein, the term 'apposition' refers to the wound edges being side-by-side and specifically to the wound edges being brought together by the vacuum force applied by the suction device such that the tissue edges are in apposition (side-by-side).

As used herein, the phrase 'manual control' refers to a user who adjusts a control sensor that is monitored by the processor, which thereby adjusts one or both the vacuum device and the suction device settings. In an embodiment of the invention, the suction device can deliver an analgesic and the user can be a patient who can self-administer the analgesic by adjusting a control sensor. In an alternative embodiment, a medical technician can administer an agent while the suction device is being operated by a physician.

In the following description, various aspects of the present invention will be described. However, it will be apparent to those skilled in the art that the present invention can be practiced with only some or all aspects of the present invention. For purposes of explanation, specific numbers, materials, and configurations are set forth in order to provide a thorough understanding of the present invention. However, it will be apparent to one skilled in the art that the present invention can be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes. Furthermore, it will also be apparent that the present invention is not limited to any particular software programming language or programming paradigm.

Systems and methods in accordance with embodiments of the present invention can provide for improved presentation and interaction with digital content and representations of digital content. Representation as used herein includes, but is not limited to, any visual and/or audible presentation of digital content. By way of a non-limiting example, digital images, web pages, digital documents, digital audio, and other suitable content can have corresponding representations of their underlying content. Moreover, interfaces such as graphical user interfaces can have corresponding representations of their underlying content.

The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

The treatment of open wounds too large to spontaneously close have long been a troublesome area of medical practice. The initial stage of healing is characterized by the formation of granulation tissue which can take several hours. When an open wound is present or formed during surgery, it is not feasible to wait for normal wound healing. In order to help address this situation, application of vacuum has been proposed as a sealing device for the abnormal tissue. If a tissue displays a site which is bleeding, a suction cup can be applied at that site to tamponade active bleeding until the surgery can progress sufficiently to repair or remove the structure in question.

When a vacuum is applied to a suction cup on a structure having a blood flow, blood can typically pool inside the site, which can lead to the formation of a hematoma. When an obstetrical vacuum extractor is applied to a fetal scalp during vacuum extraction-assisted deliveries of newborns, for example, occasionally a small bruise or hematoma occurs on the scalp. Additionally, some soft tissue edema and swelling can occur on the area of the scalp where the vacuum was applied.

There is a significant need for vacuum-assisted devices in surgical and obstetrical delivery procedures. For example procedures that involve the use of vacuum cups, grasping cups, a tamponade apparatus, or suction cups that attach to body tissue require the use of external vacuum generation pumps. In an embodiment of the present invention, the levels of harmful chemicals in the air affecting a patient or circulating in a patient's blood stream can be detected and used to modify the pressure and or vacuum applied during a procedure. In an embodiment of the present invention, the level of analgesia in a patient can be detected and used to modify the pressure and or vacuum applied during a procedure. In an embodiment of the present invention, compression in a wound or compression in tissue can be detected and used to modify the pressure and or vacuum applied during a procedure. In an embodiment of the present invention, the compression can be in an area proximal to the wound. In an embodiment of the present invention, the compression can be in an area remote from the wound. In an embodiment of the present invention, by selecting tissue apposition of wound edge through compression the congealing of blood in a wound can be increased.

In an embodiment of the present invention, the device enables a patient to self medicate. In an embodiment of the present invention, the pressure and or vacuum applied during a procedure is tied to contraction. Because there is a finite time of contraction, this enables a physician to be able to make the best use of the limited time.

In an embodiment of the present invention, the vacuum collapses the suction cup administering a drug; by monitoring for the physiologic response to the drug the pressure and or vacuum can be modulated to control drug delivery. In an embodiment of the present invention, voice control and voice recognition based response can be used to control the pressure and or vacuum applied during a procedure.

In an embodiment of the present invention, visual recognition of cup position can be used to give feedback of delivery of an agent. As the vacuum collapses the suction cup the agent is brought into contact with the tissue and administration begins/increases. Computer recognized visual reconstruction of the position of the cup can be used to give feedback regarding delivery of the agent.

In an embodiment of the present invention, the pump, can be used with vacuum devices that support the delivery of active agents as disclosed in U.S. patent application Ser. No. 13/450,464 to Lonky et al. which is herein expressly incorporated by reference in its entirety. In an unexpected result, it was found that the delivery of active agents can be facilitated by concurrent use of vacuum (negative pressure) and positive pressure. In an embodiment of the present invention, the negative pressure can be used to provide grasping force and the positive pressure can be used to enhance delivery of an active agent to the wound site tissue. By monitoring the applied vacuum pressure, the pump can determine by way of pre-programmed pressure limits or the maintenance of a vacuum condition, that agent delivery can be commenced. Grasping devices can be configured with integral agent storage compartments or can utilize external agent containers fit to the suction device. Positive pressure provided by the pump port 207 can be connected to the agent holding chamber or device whereby the application of pressure can improve release of the agent at the tissue site. Agent release can be performed using metered pressure pulses: controlled by programmed parameters or by profiles determined by and dependent upon external sensor data. Agent delivery can also be performed as a single dose application event.

Before describing the invention in detail, it is helpful to describe an example environment in which the invention can be implemented. The present invention is particularly useful in obstetrical delivery where the surgical procedure requires that a grasping cup or suction cup be attached to the fetal skull during the obstetrical delivery. Under these circumstances, monitoring of the suction cup can be partially obscured as the cup is attached in utero during the second stage of labor. The presence or absence of hair on the fetus scalp, the weight of the fetus and amount of fatty tissue on the scalp, the position of the fetus in the womb and the location that the suction device 435 is applied to the fetus scalp can all affect the effectiveness of this pumping device 301 and the procedure for its use. In this manner, the pumping device 301 can considerably assist the surgeon. The surgeon is able to diagnose on a continually unfolding basis the important features affecting the delivery procedure in a timely and accurate fashion and use this diagnosis to set appropriate vacuum levels for the pumping device 301. Further, the ability of the surgeon to be able to make use of real-time changes to the delivery procedure in changing the vacuum levels applied to the pumping device 301 to maintain the fixed vacuum to the suction device 435, can allow the surgeon to compensate for many of the variations related to these important features. Often, a nurse or assistant will operate the hand vacuum pump away from the operative delivery field while the physician gives verbal commands to activate and release the pump pressure but has no direct oversight. The physician simultaneously focuses on the timing and intensity of the traction force needed to extract the fetal head from the birth canal. Thus the physician is not continually regulating and monitoring the vacuum pressure which can pose a safety hazard and affect the ability of the cup to remain attached to the fetal scalp during delivery, resulting in a "pop off" of sudden release of the cup from the application site.

Surgical and obstetrical delivery procedures require suction devices 435 including vacuum cups, grasping cups, a tamponade apparatus, or other fixtures that attach to body tissue. Each of these devices requires a vacuum be applied to attach the device to tissue. The vacuum can be applied by a pump. Further, these procedures require continual monitoring, manipulation and re-activation of the pump by the physician. As such, the monitoring and manipulation create additional workload that distracts the physician from the primary surgical task.

Suction devices to manipulate tissue during surgery have exhibited various disadvantages. The suction devices are difficult to utilize in that the surgeon has very little control over the level of vacuum applied to the tissue. There is a check release valve on the hand-held pump, and the surgeon has the ability to re-pump up the vacuum. However, these tasks are difficult when the physician is concentrating on other facets of the surgical procedure. Importantly, the surgeon's ability to monitor the vacuum level that is applied through a suction cup and fine tune manipulations to increase or decrease vacuum pressure is very imprecise. Further, although the hand pumps can include a gauge, the physician does not have the time to visually monitor the gauge. More importantly, even if the physician had the ability to visually monitor the pressure of the gauge, the physician's manual reflexes would not allow the physician to react to the pressure fluctuations in time to avoid, for example, separation of the suction device. In an embodiment of the invention, the vacuum can prevent separation at the margin, i.e., at the suction device rim contact site. Further, releasing the vacuum on the tissue can only be carried out by releasing the check relief valve. Moreover, manipulation of the tissue using the suction device is limited by the direct application of force along the tube. In addition, the field of movement is not versatile, and can be inadequate for purposes of a given surgery. Additionally, applying the vacuum requires the assistance of a second medical professional.

A vacuum of atmospheric pressure is 1 atmosphere=760 torr. Generally, "approximately" in this pressure range encompasses a range of pressures from below $7.6 \times 10^3$ torr to $7.6 \times 10^1$ torr. A pressure of below $10^{-3}$ torr would constitute a high vacuum. A pressure of below $10^{-2}$ torr would constitute a medium vacuum. A pressure between atmospheric pressure and a medium vacuum constitutes a low vacuum. In an embodiment of the invention a vacuum is sensed at a suction device 439. In an alternative embodiment of the invention a vacuum is sensed at a wound 510. In another embodiment of the invention a vacuum is sensed at a tissue. In an embodiment of the invention the vacuum sensed at the tissue compensates for out-gassing and leaks when the suction device is applied to the tissue. Generally, "approximately" in a low vacuum pressure range encompasses a range of pressures from between $5 \times 10^{-1}$ torr to $5 \times 10^{-2}$ torr. Generally, "approximately" in a medium vacuum pressure range encompasses a range of pressures from between $5 \times 10^{-2}$ torr to $5 \times 10^{-3}$ torr. In an embodiment of the invention, a marginal increase in vacuum is an increase of vacuum from $10^{-1}$ torr to $5 \times 10^{-2}$ torr. In an alternative embodiment of the invention, a marginal increase in vacuum is an increase of vacuum from $5 \times 10^{-2}$ torr to $10^{-2}$ torr. The pumping device can operate to lower the pressure from atmospheric pressure to generate a high vacuum. In an embodiment of the invention, a low vacuum can be applied in for example obstetric suction devices. In an embodiment of the invention, a medium vacuum can be applied in for example orthopedic suction devices. In an embodiment of the invention, immediate release of a low vacuum reduces the vacuum to approximately atmospheric pressure in between a lower limit of approximately 0.1 second and an upper limit of approximately 0.5 second. In an embodiment of the invention, immediate release of a medium vacuum reduces the vacuum to approximately atmospheric pressure in between a lower limit of approximately 0.3 second and an upper limit of approximately 1.0 second. In an embodiment of the invention, a force of approximately $10^2$ Newton can be applied to tissue with the pumping device 301 through a suction device 439. In an alternative embodiment of the invention, a force of approximately $10^3$ Newton can be applied to tissue with the pumping device 301 through a suction device 439.

In various embodiments of the invention, the pumping device can allow grasping of structures through a suction device during various types of surgery. Any organ or structure that has a smooth surface to which a pumping device can attach and manipulate can be a candidate for use with the pumping device. U.S. Pat. No. 6,641,575 "Surgical Vacuum Instrument for Retracting, Extracting, and Manipulating Tissue" by Neal M. Lonky, which is explicitly incorporated by reference in its entirety, outlines an "open cup grasper" suction device 435 as envisaged in various embodiments of the invention attached to the pumping device 301. The "open cup graspers" can be adapted for use with the pumping device for open abdominal (laparotomy), chest (thoracotomy), brain (craniotomy) or orthopedic uses (vacuum traction or manipulation of bony surfaces). In addition, there is a more retroperitoneal surgical approach that can benefit from the pumping device 301. Urology surgeons use an incision in the back to get to the kidneys. During this surgery the kidneys or other surfaces can be manipulated using the pumping device. U.S. Utility application Ser. No. 12/690,763 "Portable Regulated Vacuum Pump for Medical Procedures" filed Jan. 20, 2010 is also explicitly incorporated by reference in its entirety.

Unexpectedly, it was found that application and maintenance of a fixed constant vacuum from a pumping device prevented separation of the margin of the suction device from tissue when traction was applied or when patient movement jarred the margin of the device in the setting of tamponade of a bleeding site. In particular, it was found that the degree and range of motion, and amount of force which could be applied in traction, extraction, tamponade, and manipulation were all enhanced by the application of a constant vacuum.

In discussions with surgery assistants during procedures where only the hand pump was available to a number of surgeons, it became apparent that a mechanical pump led to procedural failures due to surgeon fatigue. The effort required in constantly monitoring the pressure gauge and reinitiating the mechanical pumping by grasping and compressing the handle exacerbated psychological pressure and physical fatigue due to the surgical procedure. In experiments with an animal model or simulations with human tissue it was observed that "pop off" detachments were significantly minimized with the automated pumping device 301 (see FIG. 3). This result was unexpected based on the informal questioning of a group of five surgeons who were shown a prototype pumping device 301 in these model or simulation environments. This result was also unexpected inasmuch as all surgeons consulted indicated that they did not know marginal separation was a factor that could be addressed by a constant vacuum pump until shown the prototype and/or the results.

If traction force exceeds the pressure under the suction device (the attachment force), the suction device edge furthest from the traction point will lift and separate from the tissue, causing the leakage leading to cup "pop off". Essentially, when that equilibrium is reached and the two pressures equilibrate, there is a slow leak. It was learned after consulting with surgical assistants that the surgeon does not sense this release and thereby cannot manually pump the hand-held vacuum pump to counteract the leakage in time before the suction device releases completely. Unexpectedly, it was found that a machine-driven pump sensor can detect the release as measured by the drop in vacuum, and compensate for the release by activating the automated pump and compensating for the partial release, thereby allowing application of greater traction force without experiencing "pop off".

Figure 4:
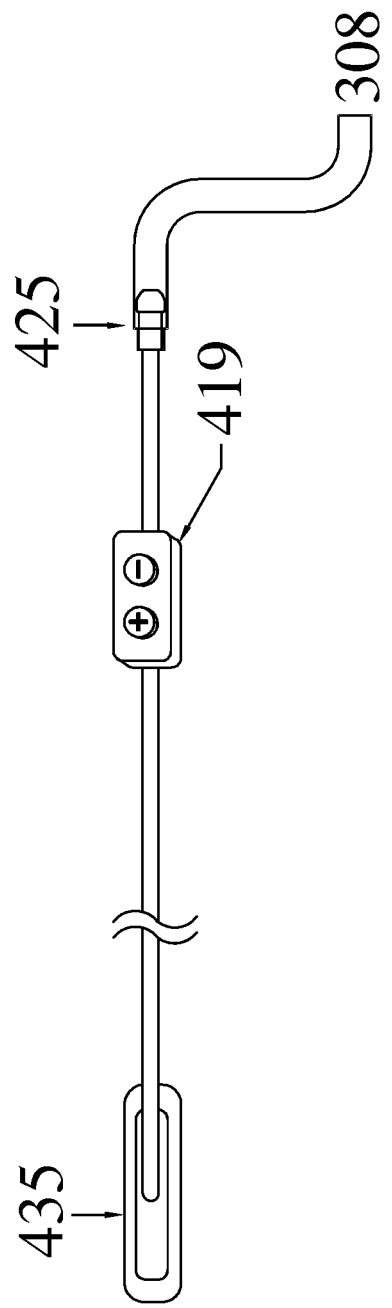
FIG. 4 is a top view of a wireless control unit 419 with two buttons in accordance with an embodiment of the invention for controlling the pumping device 301 and applying a vacuum to a suction device 435.
Figure 5:
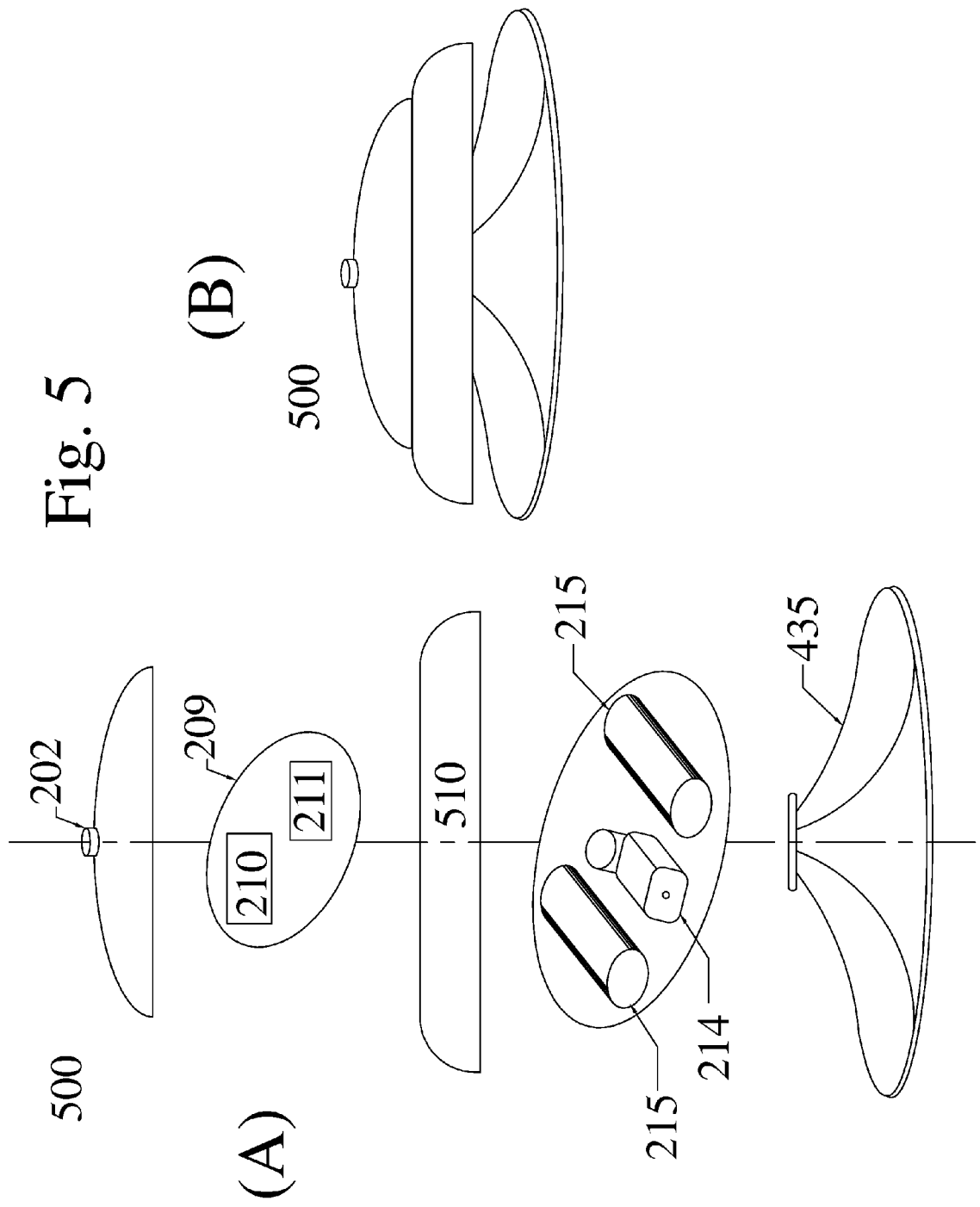
FIG. 5A is a disassembled integral suction and pumping device 500 ready for assembly in accordance with an embodiment of the invention.
FIG. 5B is an assembled integral suction and pumping device 500 in accordance with an embodiment of the invention.

When a suction device 435 is applied to a fetal scalp on which lanugo, vellus or terminal hair is present, the hair can disturb the seal between the suction device and the scalp and thereby result in a vacuum leak (see FIGS. 4-5). Application of a constant vacuum can compensate for the vacuum leak allowing for traction, extraction, and manipulation of the fetal head. Once the head has exited the vagina the surgeon needs to be able to release the suction device and manually deliver the fetus. Complete venting of the relief valve 221 via a solenoid allows instantaneous release of the suction device 435. When a suction device is applied to an organ containing an uneven or obstructed tissue surface, the uneven surface can result in a vacuum leak. Application of a constant vacuum can compensate for the vacuum leak allowing for traction, extraction, and manipulation of the organ. If the systolic to diastolic pressure gradient is small and a pulse pressure is created, the blood might circulate (exit and re-enter) the wound site. Such flow would allow admixture of medications or other substances placed inside the cup cavity into the wound site.

Application of a suction device at a tissue site which is bleeding, with a constant vacuum, i.e., an applied vacuum that compensates for the changed clotting behavior of the wound with time, can allow enhanced clotting and cessation of the bleeding from the site. It could be expected that a pumping device with a vacuum tube delivering a vacuum to a suction device applied to the wound would accelerate the flow of blood. Contrary to this preconceived idea, application of vacuum constricts the tissue at the margin of the bleeding site into/toward the bleeding site. As a result, the margin collapses, allowing pooling of blood and clotting factors aiding clotting and cessation of blood flow.

In an embodiment of the invention, the timing and periodicity of the application of the vacuum can be applied in a pulsatile flow opposite that of a patient's pulse. In an embodiment of the invention, the vacuum can be applied to tissue. The tissue can include, epithelial layers, organs, osseous tissue, bony tissue and connective tissue exposed by an open incision during a laparotomy, thoracotomy, craniotomy, retroperitoneal surgery and orthopedic vacuum traction or manipulation of bony surfaces. In an embodiment of the invention, the vacuum can be applied to a wound when the surgeon senses diastoly to more actively collapse the wound. The wound can be one or more of a subcutaneous hematoma, an incision made by the surgeon, a site of removal of tissue by the surgeon, a site of removal of an organ made by the surgeon, one or more puncture holes being treated by the surgeon or one or more laceration sites being treated by the surgeon. Treating the wound can include stopping the blood flow from a site, reducing the blood from a site, assisting in the arrest of the flow of blood to a site, stopping the blood flow to a subcutaneous hematoma, reducing the blood flow to a subcutaneous hematoma, assisting in the arrest of the flow of blood to a subcutaneous hematoma limiting its size and scope. In an embodiment of the invention, the vacuum can be increased to the wound when the surgeon senses diastoly to more actively collapse the wound. In effect the surgeon can use the patient's own tissue and the suction device as a tourniquet and the vacuum can be increased to tighten the tourniquet. In an embodiment of the invention, marginally increased vacuum pressure can be applied in diastoly, and thereby more easily applied, and then the vacuum can be maintained to overcome the systolic pressure pulse, thus slowing or arresting the flow of blood.

In an embodiment of the invention, the vacuum can be adjusted to compensate for the pulse pressure variation, maintaining or slightly exceeding the suction device vacuum against the higher systolic pressure to secure placement at or over the bleeding site. Maintenance of the suction device on the bleeding site will ultimately more actively collapse the wound. In various embodiments of the invention, the pumping device 301 can increase or decrease the vacuum to the wound in synchronization with a patient's heart changing from diastol to systoly to more actively collapse the wound. In this manner, the clotting and cessation of blood flow of a wound can be further improved. It was unexpected that vacuum constriction applied when the patient's blood pressure is low could reduce bleeding. It was also unexpected that a surgeon would be able to simultaneously perform surgery and monitor the pulse pressure. In simulations of a bleeding site event that were carried out on five separate occasions with five different surgeons, each surgeon reported in an interview after the simulation that they were able to simultaneously perform the surgery and monitor the pulse pressure.

Further, it is noted that undetected vacuum loss can result in the untoward premature detachment of the vacuum cup device from the body surface under manipulation. Improper or negligent operation of the vacuum pump, or the manipulation of the tissue in contact with the various procedure cups/devices, can hamper the medical procedure or damage the affected tissue.

In the past, vacuum assisted devices or vacuum generating devices have not recorded or maintained a record of operation of parameters including the applied vacuum, vacuum leak being compensated, time of application, temperature, change in conditions during procedure, or notes regarding the classification of the surface and the nature of the problem addressed that can be reviewed and archived for inclusion in medical records. As such, these vacuum assist devices do not allow the physician to utilize insight and intuition to choose conditions for the procedure that are similar to conditions previously utilized. Finally, these vacuum assist devices do not allow the surgeon to select conditions based not only on the similarity of the procedure but also based on the surgeon performing the procedure.

Post-surgical examination of the parameters used during a number of surgical procedures including vacuum applied, nature of tissue, evenness of surface, vacuum leak due to uneven surface, force of extraction/manipulation applied, time duration of vacuum applied and variation of vacuum applied, allow review and establishment of guidelines that advance the safety and efficacy of the various surgical procedures being undertaken for a given patient sub-population. By recording all the data obtained during surgery pertaining to the use of the pumping device 301 and making this data available together with other details of the patient and the operating surgeon, a surgeon can store useful data and proactively select parameters for future use in similar circumstances based on stored data. For example, ultrasound analysis of the fetus prior to birth can be performed to determine how much hair is present on the fetal scalp. This information can be used to select appropriate conditions for use in the childbirth, should a suction device be required. In addition to the absence or presence of hair and the relative amount of hair, the surgeon can also select the size and type of the specific suction device 435, and the specific type of pumping device 301, based on the performance characteristics of the specific suction device 435, and the specific type of pumping device 301. During specific surgical procedures a variable vacuum can be desirable, where the vacuum applied to the suction device 435 is varied depending on the stage of the surgical procedure. In such circumstances, the surgeon can manually indicate the different stages of the surgical procedure through a single depression of a control unit 419 button or through voice-activated recognition and response by the pumping device 301. In an alternative embodiment of the invention, the different stages of the surgical procedure can be communicated to or noted by an assistant who enters the appropriate information in the pumping device 301. In an embodiment of the invention, the control unit 419 is attached to the suction device 439. In an embodiment of the invention, the control unit 419 can be held by the surgeon while holding and controlling the suction device 439. In an embodiment of the invention, the control unit 419 can be held by the surgeon with the same hand holding and controlling the suction device 439.

In various embodiments of the present invention, an electromechanical compact pump provides a sustained vacuum force to a variety of suction devices 435 applied to body tissue and surfaces for the purpose of grasping, manipulating, tamponade, and/or traction of body parts of a patient or a fetal skull during obstetrical delivery. In an embodiment of the present invention, the vacuum can be automatically regulated and monitored continuously by the pumping device 301 to effect the uninterrupted generation of a constant vacuum pressure to prevent untoward release of the suction device from the affected body part or tissue. In an embodiment of the present invention, the vacuum can be automatically regulated and monitored continuously by the pumping device 301 to effect the uninterrupted generation of a variable vacuum pressure to prevent untoward release of the suction device 435 from the affected body part or tissue. In an embodiment of the present invention, the desired vacuum provided by the pumping device 301 can be preset by the operator and can be adjusted by the surgeon as necessary during a medical procedure. In an embodiment of the present invention, an electronic record of the vacuum pressure(s) vacuum leak, and time duration of the vacuum can be stored internally within the device. In an embodiment of the present invention, the electronic records can be retrieved by an accessory memory transfer device or transmitted by wired or wireless (RF/IR frequency) connection to an external computer or other receiving equipment (i.e. printer, mass storage device). In an embodiment of the present invention, the pumping device 301 can operate as a primary vacuum pump. In an embodiment of the present invention, the pumping device 301 can assist continuously or during designated times in parallel with existing hand-operated vacuum pumps. In an embodiment of the present invention, the pumping device 301 can operate as a back-up vacuum pump in parallel with existing hand-operated vacuum pumps.

In various embodiments of the present invention, improved and unique operation is provided when compared to non-regulated vacuum pumps. In an embodiment of the present invention, the pumping device 301 includes an electromechanical pump (electro-vacuum pump). In an embodiment of the present invention, the pumping device 301 is hand held. In an embodiment of the present invention, the pumping device 301 is portable. An electro-vacuum pump for assisting or regulating the vacuum obtained by hand-operated pumps has not previously been proposed or used. In an embodiment of the present invention, the pumping device 301 improves performance of hand-operated pumps currently in use by providing sustained and regulated vacuum. In an embodiment of the invention, the surgeon selects the desired vacuum by applying the vacuum with a hand-held pump and the pumping device 301 is used to maintain this pressure. In an embodiment of the present invention, the vacuum regulation provided by the invention prevents untoward release ("pop-offs") of grasping cups and other suction devices 435 by automatically compensating for air leaks at the interface between the grasping cup and the adhered surface, or between the grasping cup and the pumping device 301.

Figure 2:
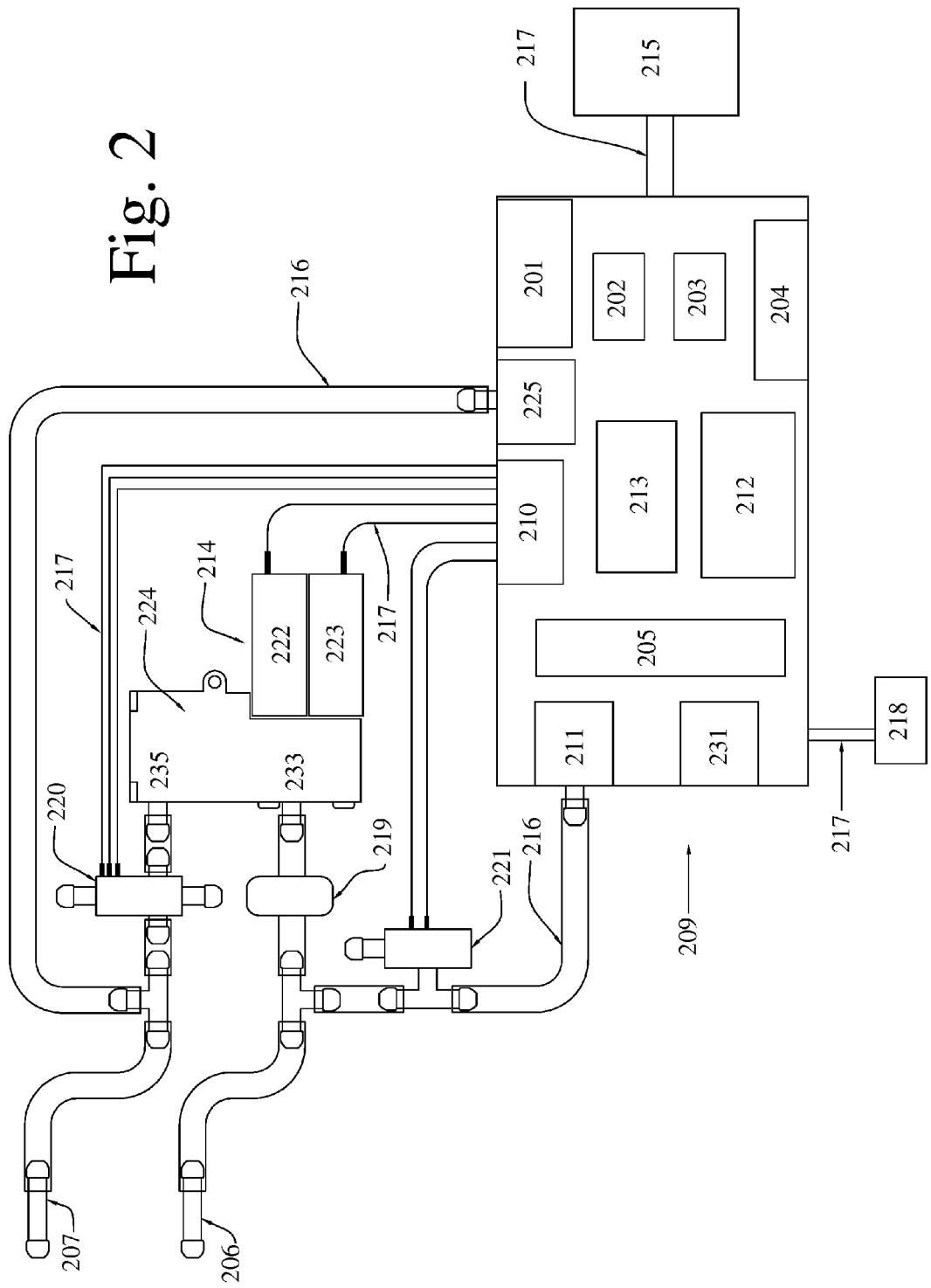
FIG. 2 illustrates the components of a circuit 209 and vacuum pump 214 for use in a pumping device 301, in accordance with an embodiment of the invention.
Figure 3:
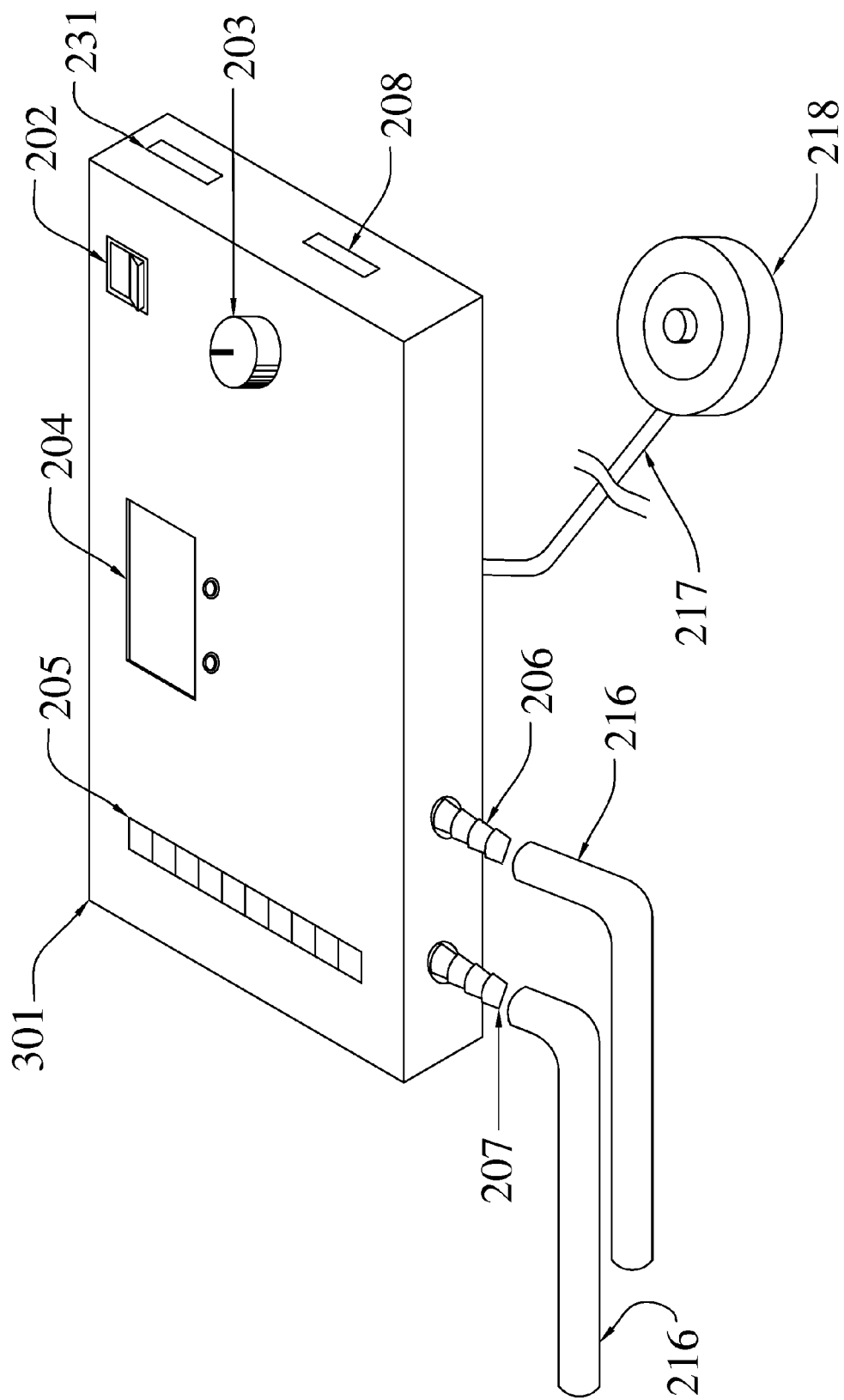
FIG. 3 is a pumping device 301 in accordance with an embodiment of the invention that can be used to implement the flowchart of FIG. 1.

In various embodiments of the invention, the portable regulated pumping device 301 shown in FIG. 3 is a self-contained vacuum-producing device that provides preset regulated pressure(s) and electronically stores operational performance data for retrieval by external means. The circuit for the pumping device is shown schematically in FIG. 2. The power switch 202 activates the pumping device 301 for operation utilizing the energy storage device 215. In an embodiment of the present invention, the power switch 202 remains indefinitely in whichever state it is placed. In an embodiment of the invention, the pumping device is activated by contact between the suction device and tissue. In an embodiment of the present invention, the vacuum selector switch 203 is a multiple position on-off switch that remains indefinitely at whichever position is selected. In an embodiment of the present invention, the vacuum selector switch 203 can provide three (3) positions. In an embodiment of the present invention, the vacuum selector switch 203 can provide ten (10) positions. In an embodiment of the present invention, the vacuum selector switch 203 can provide any number of positions between a minimum of three (3) positions and a maximum of ten (10) positions. In an embodiment of the present invention, the vacuum selector switch 203 can provide two (2) positions. In an embodiment of the present invention, the vacuum selector switch 203 can provide more than ten (10) positions. In an embodiment of the invention, the vacuum selector switch 203 can be used to select a "maintain" vacuum setting, wherein a vacuum generated by a hand-held vacuum pump is maintained by the electro-vacuum pump during the surgical procedure. In an embodiment of the present invention, the vacuum selector switch 203 position can be selected based on the surgical procedure being undertaken. In an embodiment of the present invention, the vacuum selector switch 203 position can be selected based on the identity of the surgeon performing the surgical procedure.

FIGS. 2-4 depict objects as logically separate. Such depiction is merely for illustrative purposes. It will be apparent to those skilled in the art that the objects portrayed in FIGS. 2-4 can be arbitrarily combined or divided into separate software, firmware or hardware components. Furthermore, it will also be apparent to those skilled in the art that such objects, regardless of how they are combined or divided, can execute on the same device or can be distributed among different devices connected by one or more connections.

In an embodiment of the present invention, the operator display and control 204 can be comprised of an alpha-numeric display panel and associated push-button controls to effect the change and selection of displayed captions and data. In various embodiments of the present invention, the display panel can be an LCD (liquid crystal display), LED (light emitting diode), electro-luminescent or any other component used to provide visual text or graphical representation of the pumping device's 301 operational condition, current or stored in memory. In an embodiment of the present invention, the push-button controls can be typical momentary switches such as membrane, snap-dome, or any other mechanically actuated switch. In an embodiment of the present invention, the operator display and control 204 are attached to the device circuit board 209 and are interfaced to the device processor circuitry 213 for control.

In an embodiment of the present invention, the LED bargraph indicator 205 can be comprised of multi-color LEDs or any other illuminating display device(s) that provide a sequential lighted indicator. In various embodiments of the present invention, any number of indicators can be used. In an embodiment of the invention, ten indicators can be used. In an embodiment of the invention, the indicators can use green, yellow and red colors to indicate a displayed parameter. In an embodiment of the invention, green indicators can be used at the bottom extending past the middle followed by yellow, with the red color at the top section of a vertically arranged stack of indicators.

In an embodiment of the present invention, the vacuum attachment port 206 can be a barbed hose stem made of any resilient material such as metal or plastic, or other flexible or rigid polymer. In various embodiments of the present invention, the length and diameter of the vacuum attachment port 206 can be any size. In an embodiment of the invention, the vacuum attachment port 206 extends approximately five (5) mm in length from the pumping device 301 and is two (2) mm in diameter. In an alternative embodiment of the invention, the vacuum attachment port 206 extends approximately twenty five (25) mm in length from the pumping device 301 and is six (6) mm in diameter. In an embodiment of the invention, an external suction device 435 can be connected to the pumping device 301 at the vacuum attachment port 206 location via the vacuum assisted device tubing 216. In an embodiment of the invention, a Positive Pressure Supply 222 can be connected to the pumping device 301 at the Positive Pressure Attachment Port 207 location via the vacuum assisted device tubing 216. A pressure sensor 225 within or associated with the pumping device 301 measures the pressure at or near the pumping device 301 via the vacuum assisted device tubing 216. An external sensor port 231 within or associated with the pumping device 301. In an embodiment of the invention, the external sensor port 231 can monitor the tocodynamometer contractions. In an embodiment of the invention, the external sensor port 231 can measure fetus', mother's or patient's heart rate. In an embodiment of the invention, the external sensor port 231 can measure the fetus', mother's or patient's blood pressure.

In an embodiment of the present invention, the external memory and interface port 201 can be an electrical connector used for small computer communication interfaces. The external memory and interface port 201 can be an RS-232, RS-422/485, Ethernet or Universal Serial Bus (USB) connector. The interface port 201 can provide for the wired connection of the pumping device 301 to external peripherals including personal computers, printers or other portable computing devices such as personal digital assistants (PDA), mass storage devices, flash memory devices (thumb drives) or digital telecom devices such as cellular telephones.

In an embodiment of the present invention, the vacuum assisted device tubing 308 can be a section of flexible tubing of surgical quality manufactured of any typical material such as PVC, rubber (natural or synthetic), silicone or others. The tubing 308 can be any length or diameter necessary to provide for the inter-connection of external vacuum assisted devices to the vacuum attachment port 206. As shown in FIG. 4, the vacuum assisted device tubing 308 can have identical or differing internal or outer diameters (ID and OD) that facilitate connection to a suction device 435 or other target medical device that requires vacuum pressure for operation.

In an embodiment of the present invention, the device circuit board 209 holds the electronic components for the pumping device 301 system control. The operator display and control 204, LED bargraph indicator 205, external memory and interface port 201, pump control circuitry 210, vacuum sensor 211, wireless communications circuitry, and the device processor circuitry 213 can be attached to the circuit board 209. The device circuit board 209 can be externally powered by the energy storage device 215.

In an embodiment of the present invention, the pump control circuitry 210 can be comprised of typical electronic components to effect the switching of power to the vacuum pump 214. These components include, but are not limited to: electromechanical relays, transistors, MOSFETS, diodes, or other devices capable of controlling the electrical current necessary to power the vacuum pump 214. The pump control circuitry 210 can be controlled through an interface with the device processor circuitry 213.

In an embodiment of the present invention, the vacuum sensor 211 can be a semiconductor device utilizing typical variable resistance or capacitance technologies that provides a proportional voltage signal output based upon the vacuum pressure applied to the sensor. The vacuum sensor 211 voltage signals can be interfaced to the device processor circuitry 213 to provide real-time vacuum pressure readings necessary to regulate the vacuum pump 214 operation.

In an embodiment of the present invention, the wireless communications circuitry 212 can provide modulated waveform signals in either the infrared (IR) or radio frequency (RF) signal range. In an embodiment of the invention, the wireless communications circuitry 212 can provide RF inputs/outputs. The modulated signals can be transmitted using any typical small computer Ethernet system WiFi standard such as EIA-802.11G, Bluetooth® methodology or discrete signaling utilizing a non-linear code encryption algorithm for secure control. The wireless communications circuitry 212 can be controlled through an interface with the device processor circuitry 213 to provide remote control and data transfer between the pumping device 301 and peripheral devices as: remote control units (pushbuttons, foot switches), personal computers, printers or other portable computing devices such as personal digital assistants (PDA), mass storage devices, or digital telecom devices such as cellular telephones.

In an embodiment of the present invention, the device processor circuitry 213 can be comprised of typical microprocessor electronic components necessary to provide pre-programmed and user-selected operation of the portable regulated pumping device 301. In various embodiments of the present invention, components of the processor circuitry 213 include but are not limited to: volatile and non-volatile memory, real-time clocking, and peripheral interface and logic devices. In an embodiment of the present invention, an internal system processor firmware program can provide the direction to operate the various circuit blocks that reside on the device circuit board 209. Functionality provided by the firmware can include:

a) comparison of desired and actual vacuum pressure supplied by the pumping device 301 to the user-selected suction device 435. In an embodiment of the present invention, a control algorithm can be used to control hysteresis and dwell (see FIG. 6(A)) and thereby minimize or eliminate oscillatory cycling of the vacuum pump 214 that: minimizes pump run duration time, maintains vacuum pressure within a desired range, and minimizes power consumption;

b) activation of the pump control circuitry 201 to control the vacuum pump 214 to reach and maintain the user-selected vacuum pressure;

c) logic output signal control to effect a proportional indication of the vacuum sensor 211 signal at the LED bargraph indicator 205;

d) interface logic for the operator display and controls 204 to provide user adjustments of the pumping device 301 and to provide status messaging and data during operation;

e) control of the wireless communication circuitry 212 to implement the properly formatted exchange of data with other peripheral devices; and f) control of the external memory and interface port 201 to provide the proper transfer of stored histogram data to external memory storage devices, and the bi-directional communication required to effect remote control of the pumping device 301 using an external host computing device.

In an embodiment of the present invention, the vacuum pump 214 can be a miniature pump utilizing any typical pressure building chamber-type mechanism such as diaphragm, bellows, piston or WOB-L® technology. FIG. 2 shows an embodiment of the invention where the vacuum pump 214 includes one or more pump motors for supplying negative pressure 223 and for supplying positive pressure 222 connected to a pump head 224. In an embodiment of the present invention, the pump motor can be a rotational electromechanical type. In an alternative embodiment of the present invention, the pump motor can be of a reciprocating electromechanical type. In an embodiment of the present invention, the pump motor can use an alternating current (AC) electrical power source. In an alternative embodiment of the present invention, the pump motor can use a direct current (DC) electrical power source.

In an embodiment of the present invention, the energy storage device 215 can be a DC energy or charge storage device that is configured to provide power to the device circuit board 209. The energy storage device 215 can include any battery or cell known in the field, including general purpose batteries, alkaline batteries, lithium ion batteries, nickel-cadmium batteries, nickel metal hydride batteries, lead acid batteries, deep cycle batteries, rechargeable batteries, or any other batteries. In an embodiment of the invention, the voltage or energy content of the energy storage device 215 is in the range from a minimum voltage of approximately six (6) volts to a maximum voltage of approximately twenty four (24) volts. In an embodiment of the invention, the voltage or energy content of the energy storage device 215 is in the range from a minimum voltage of approximately nine (9) volts to a maximum voltage of approximately eighteen (18) volts. In an embodiment of the invention, the voltage or energy content of the energy storage device 215 is approximately twelve (12) volts.

In an embodiment of the present invention, the flexible tubing 216 can be flexible tubing of surgical quality manufactured of any typical material such as PVC, rubber (natural or synthetic), silicone or others. The flexible tubing 216 can be sized to provide an airtight connection between the vacuum pump 214, the vacuum sensor 211, the check valves 219, 220 the solenoid relief valve 221, the pressure sensor 225, the vacuum attachment port 206, and the Positive Pressure Attachment Port 207.

In an embodiment of the present invention, the wiring 217 can comprise a current-conducting material that electrically connects the components of the pumping device 301. The wiring 217 can include any material or wiring known in the art, including but not limited to copper and other metals having low electrical resistance. The wire gauge can be chosen to reduce costs while simultaneously carrying current with a minimum of resistant power dissipation.

In an embodiment of the present invention, a foot switch 218 can be used with the pumping device 301. In an embodiment of the present invention, the foot switch 218 can be a push-on/push-off latching switch that remains in the last selected position indefinitely. The foot switch 218 can be electrically connected to the pumping device 301 with a wired tether or through wireless means utilizing the wireless communications circuitry 212. The foot switch 218 can allow the vacuum pump 214 of the pumping device 301 to be operated remotely. The electrical switch mechanism is typically a mechanically actuated push-button switch; when in the 'on' condition, the vacuum pump 214 is allowed to operate. Conversely, when in the 'off' condition the operation of the vacuum pump 214 is disabled.

In an embodiment of the present invention, the wireless control unit 419 can be a small form factor self-contained RF transmitter with an integral storage battery power source. In an embodiment of the present invention, the wireless control unit 419 can be wirelessly connected to the pumping device 301 utilizing the wireless communications circuitry 212 with discrete signaling utilizing a non-linear code encryption algorithm for secure control. In an embodiment of the present invention, the wireless control unit 419 control mechanism can be comprised of two (2) or more mechanically actuated push-button switches with tactile surfaces allowing the operator to differentiate between the buttons and thereby allowing each button to be identified without visual verification. Tactile differentiation can be accomplished by unique button size, shape, embossed or raised symbols, or any combination of these methods. The wireless control unit 419 can allow the pumping device 301 to be operated remotely. Through the actuation of a single or predefined combination of buttons, the operation of the pumping device 301 can be controlled. Control functions include: vacuum pump 214 on/off, release of vacuum, real-time adjustment of regulated vacuum operating pressure and adjustment of other operating parameters as afforded by the device processor circuitry 213.

The check valve 219 can be an in-line, 2-port miniature air valve utilizing swing disk diaphragm, ball, or other seating methods typical in the art. The check valve 219 allows air flow in only one direction, toward the vacuum pump 214. Disk or ball check valves can be free moving or utilize levers or springs to assist in seating faster to eliminate air flow shock and/or inhibit air flow based upon applied vacuum. The check valve 219 can be positioned to eliminate vacuum leakage through the vacuum pump 214 when the vacuum pump 214 is not operating.

The solenoid relief valve 221 can be an electro-mechanically operated 2-port valve utilizing moving plunger or plate technology to open and close an air passage between the two air ports. Plunger or plate valve actuators can be driven by a magnetic field created when electrical current is applied to a valve coil. The solenoid coil can be AC or DC current types as typical in the art. The valve can be held in a normally-closed condition, inhibiting air flow at and through each port. Upon electrical actuation by the pump control circuitry 210, the valve can be opened allowing vacuum pressure present at vacuum attachment port 206 to be vented to the atmosphere, releasing vacuum holding pressure at the external vacuum assisted device.

FIG. 2 shows the pressure chamber of vacuum pump 214 connected on the 'IN' 233 or negative pressure outlet side through the check valve 219 to both the vacuum attachment port 206 and the solenoid relief valve 221, then to the vacuum sensor 211 through the use of the flexible tubing 216 and on the 'OUT' 235 or positive pressure outlet side through the check valve 220 to both the Positive Pressure Attachment Port 207 and the Pressure Sensor 225, through the use of the flexible tubing 216. The interconnection of these items can also be accomplished with other methods such as face to face port connections using threaded fasteners or all items can be integrated into the pump chamber housing forming a single unit requiring no external connections.

In an embodiment of the present invention, the circuitry sections on the device circuit board 209: pump control 210, vacuum sensor 211, external memory and interface 201, wireless communication 212, device processor, operator display and controls 204 and the LED bargraph indicator 205 can all be soldered in place and interconnected as required with the printed wiring that forms a part of the device circuit board 209. In an embodiment of the present invention, the vacuum pump 214 and the energy storage device 215 can be wired 217 to the device circuit board 209. In an alternative embodiment of the present invention, the vacuum pump 214 and the energy storage device 215 can be connected and soldered directly to the device circuit board 209.

In an embodiment of the present invention, the power switch 202 and vacuum selector switch 203 can be connected to the device circuit board 209. In an alternative embodiment of the present invention, the power switch 202 and vacuum selector switch 203 can be relocated with alternatively wired 217 connections.

In an embodiment of the present invention, the foot switch 218 can be wired 217 to the pumping device 301 with a cable of a suitable length to position the foot switch 218 near the operator. In an alternative embodiment of the present invention, the foot switch 218 can be used wirelessly through an RF link with the wireless communications 212 circuitry to accomplish the same functionality afforded by a wired 217 connection with the device circuit board 209.

FIG. 1 is a schematic flow diagram used to exemplify the use of an embodiment of the present invention in a surgical procedure. The pumping device 301 is initially in an 'off' state, with no power applied to the internal components. Prior to operation, the user attaches the suction device 435 via connector 425 (see FIG. 4) to the vacuum attachment port 206 of the pumping device 301 using the vacuum assisted device tubing 308 at step 110. The suction device 435 is one of one or more devices that require vacuum assistance. Then the user applies power to the pumping device 301 with power switch 202 at step 100 and positions selector switch 203 to the desired operating vacuum setting at step 105.

Figure 6A:
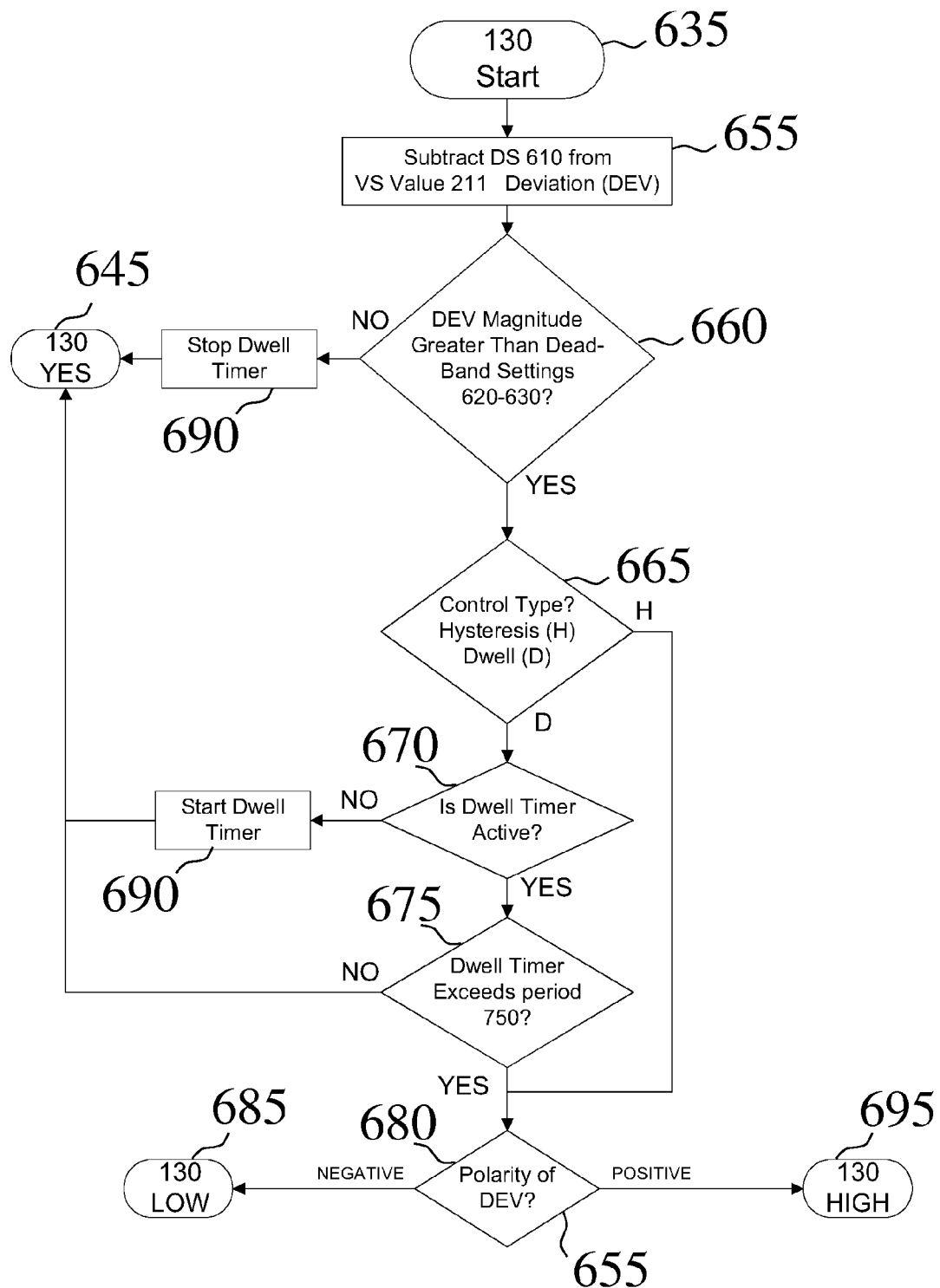
FIG. 6A is a flowchart showing the detail of decision block 130 in accordance with an embodiment of the invention.

When enabled with the foot switch 218 or the suction device control 419 (at step 115), the device processor circuitry 213 determines if the vacuum pump 214 is required to operate, or not, based upon the relationship between the user setting of the vacuum selector switch 203 and the signal magnitude of the vacuum sensor 211 (at steps 120 and 130). FIG. 6(A) shows a schematic flow diagram of decision block 130 in more detail. In an embodiment of the invention with a vacuum cup able to supply positive and negative pressure (combination cup) the control module checks for the installation of a combination cup 131 and uses positive pressure to adjust the pressure at the combination cup as required 132. Once activated the pumping device begins to monitor and store the data including the vacuum applied to the suction device, the vacuum at the vacuum pump, the vacuum loss (not shown in FIG. 1). If the vacuum sensor signal is lower than the desired vacuum, the pump control circuitry 210 is activated powering the vacuum pump 214 until the desired vacuum is reached (steps 140 and 160); as determined by the signal from the vacuum sensor 211 and the device processor circuitry 213. The relative vacuum pressure is annunciated by the LED bargraph indicator 205, with the value of the vacuum sensor 211 signal proportionately indicated by sequential LED indicator illumination from the bottom of the bargraph to the top. If the vacuum sensor signal is higher than the desired vacuum, the pump control circuitry 210 is not activated and the relief valve 221 is opened (step 150) to reduce the vacuum. If the vacuum sensor signal is within the limits the vacuum sensor continues to monitor the pressure (step 120) until the power switch 202 is turned 'off' (steps 170 and 180).

During the operation of the pumping device 301, vacuum pressure data can be stored in non-volatile memory that forms a part of the device processor circuitry 213. The vacuum pressure data can be stored sequentially with associated real-time (time of day) values that provide a direct correlation of the operating vacuum at a given time. The stored memory data can be retrieved by the user. In various embodiments of the invention, the stored memory data can be retrieved by:

(a) negotiation and data download to an external device using the wireless communication circuitry 212;

(b) insertion of a non-volatile memory device (flash/thumb drive) at the external memory and interface port 201; or (c) by request (serial communication) of a host computer connected to the external memory and interface port 201.

With the operator display and controls 204, the user can perform various functions that affect the operation of the pumping device 301; these functions include, but are not limited to:

(i) adjust dead-band (+/− error range of vacuum signal when compared to desired setting) and dwell (delay time before/after allowable error is exceeded to activate/de-activate the pump) parameters;

(ii) adjust preset vacuum values associated with the user vacuum selector switch 203;

(iii) monitor vacuum pressure in real-time with display provided in selectable engineering units including mm/Hg, bar, mbar, torr, mtorr, PSI and kPa;

(iv) retrieve and view stored time-stamped vacuum histogram values; and (v) adjust other system parameters associated with the functionality of the LED bargraph indicator 205 and communication protocols used by the external memory and interface port 201 and the wireless communication circuitry 212.

In an embodiment of the present invention, the vacuum selector switch 203 can be expanded in functionality to include: more selections (positions), factory pre-set operational values. In an alternative embodiment of the present invention, the vacuum selector switch 203 can be eliminated completely and replaced by a single pre-set or adjustable setting through the use of the operator display and controls 204. In another embodiment of the present invention, the vacuum selector switch 203 can be set according to the surgical procedure being undertaken. In an embodiment of the present invention, the minimum and maximum pressure which can be selected during the surgical procedure can be based on the surgical procedure being undertaken. In an embodiment of the present invention, the minimum and maximum pressure which can be selected can be based on the stored identity of a surgeon carrying out the procedure. The identity of the surgeon carrying out the procedure can be detected through a RFID reader in the pumping device 301 and a tag associated with the surgeon. In an embodiment of the present invention, the minimum and maximum pressure which can be selected during the surgical procedure can be restricted based on the surgical procedure being undertaken.

The functionality of the LED bargraph indicator 205 can be expanded to allow user selected indications that provide: 0-100% indication of the vacuum sensor 211 signal, scaled to provide 0-100% indication of the vacuum selector switch pre-set range, or other user selected range of indication.

Attachment of the external vacuum assisted device to the vacuum attachment port 206 can be accomplished using custom configured vacuum assisted device tubing 308 sections that are pre-fabricated and sized to provide the simple interface of devices currently used in the art.

In an embodiment of the present invention, the pumping device 301 can be reconfigured to utilize simple electronic circuit components eliminating the need for the device processor circuitry 213. Electronic circuitry that provides an analog of the processor control algorithm, which performs the hysteresis and dwell functions, can be used to provide simple dedicated operation of the portable regulated pumping device 301.

In various embodiment of the present invention, the unique operational characteristics of the pumping device 301 can be utilized with vacuum pumps 214 of any size or type by modifying the pump control circuitry 210 and the vacuum sensor 211 expanding the size and types of vacuum assisted devices that can be supported.

In an embodiment of the present invention, a pumping device 301 to enable a specified vacuum to be applied to a suction device 435 attached to tissue of a mammal, comprises a sensor for monitoring a vacuum applied to the suction device. A pump 214 for increasing the vacuum to the suction device 435. A valve 221 for immediately releasing the vacuum applied to the suction device and a control circuit. Wherein the control unit 419 controls one or more of activating the pump, opening the valve 221 and adjusting operating parameters of the pumping device. Wherein activating the pump 214 applies the specified vacuum to the suction device. Wherein opening the valve 221 immediately releases the vacuum applied to the suction device 435 to release the tissue grasped by the suction device 435. Wherein adjusting operating parameters of the pumping device modifies the specified vacuum, wherein the control circuit is positioned to be operated with the hand holding the suction device.

In an embodiment of the present invention, the pumping device 301 can be made by providing the individual electronic components that comprise the functional capability for the circuitry blocks shown on the device circuit board 209. These items can be assembled using automated or manual means to the circuit board and then soldered in place. The energy storage device 215 and the vacuum pump 214 can then be connected as shown in FIG. 2, such as by soldering the electrical connections. The flexible tubing 216 can be installed by manual means to inter-connect the vacuum related devices as represented on the drawing. The foot switch 218 can be assembled separately and can be wired directly to the pumping device 301 or provided as a wireless accessory to the pumping device 301.

In an embodiment of the present invention, to use the pumping device 301, an operator can select the suction device 435 necessary for the intended medical procedure and attach such to the pumping device 301 using the vacuum assisted device tubing 308 that can be then attached to the vacuum attachment port 206. In an embodiment of the present invention, the invention can be used as an ancillary/back-up vacuum pump, in support of hand-operated pumping devices. In an alternative embodiment of the present invention, the pumping device 301 can be used as a stand-alone primary vacuum pump.

In an embodiment of the present invention, the operator then decides the desired vacuum pressure required for the selected suction device 435 and uses either the vacuum selector switch 203 to choose an operating vacuum, adjusts the vacuum pressure selection using the functionality afforded by the operator display and controls 204 or uses the wireless control unit 419.

In an embodiment of the present invention, once the portable regulated pumping device 301 is set by the operator and powered on, the vacuum pump 214 can operate to reach and maintain the vacuum pressure setting when selected to do so by the foot switch 218 condition (on/off) or wireless control 419. In an embodiment of the present invention, the operator can monitor the relative performance of the pump and its delivered vacuum by viewing the LED bargraph indicator 205, using the indicator colors green, yellow and red to readily determine if the vacuum pressure is acceptable for the medical procedure task. In an alternative embodiment of the present invention, the operator can be apprised of the relative performance of the pump through audible signals. In an embodiment of the present invention, audible signals can be used to warn the surgeon of critical parameters throughout the surgical procedure. In an embodiment of the present invention, audible signals can be used to warn the surgeon of critical vacuum or critical vacuum in relation to time parameters. In an embodiment of the present invention, the pumping device 301, by applying a pulsating vacuum can inhibit bleeding at a wound. In an embodiment of the present invention, the pumping device 301, by applying a pulsating vacuum based on a patient's pulse can inhibit bleeding at a wound.

In an embodiment of the present invention, the vacuum pressure can be controlled based upon the occurrence and/or intensity of a labor contraction during fetal delivery. The vacuum pressure applied to a connected vacuum delivery device will be adjusted automatically to synchronize minimum and maximum applied pressure with contraction intensity. Pre-programmed or operator selected parameters for min/max pressure settings can be used to determine holding (minimum) vacuum and executing (maximum) vacuum required for the procedure. Contraction detection and force sensor data can be provided to the device directly (hard-wired sensor connection) or indirectly; through a wired or wireless data link to a fetal or contraction monitoring device.

In an embodiment of the present invention, an internal uterine pressure catheter (IUPC) can be connected to the pumping device 301 to port 231 for direct monitoring of uterine contraction occurrence and pressure. The device will use this sensor data in conjunction with internal algorithms to control applied vacuum pressure.

In an embodiment of the present invention, a data link, utilizing wired or wireless techniques, can be established with external monitoring equipment to provide uterine contraction (tocodynamometer or tocotransducer) and fetal heart-rate data to the pumping device 301. This data link can be established through standard BlueTooth, 802.11a/b/g/n Ethernet, or other widely used wireless protocols, or through wired interfaces such as EIA-232, EIA-422/485 using wired or fiber-optic connections.

Figure 6B:
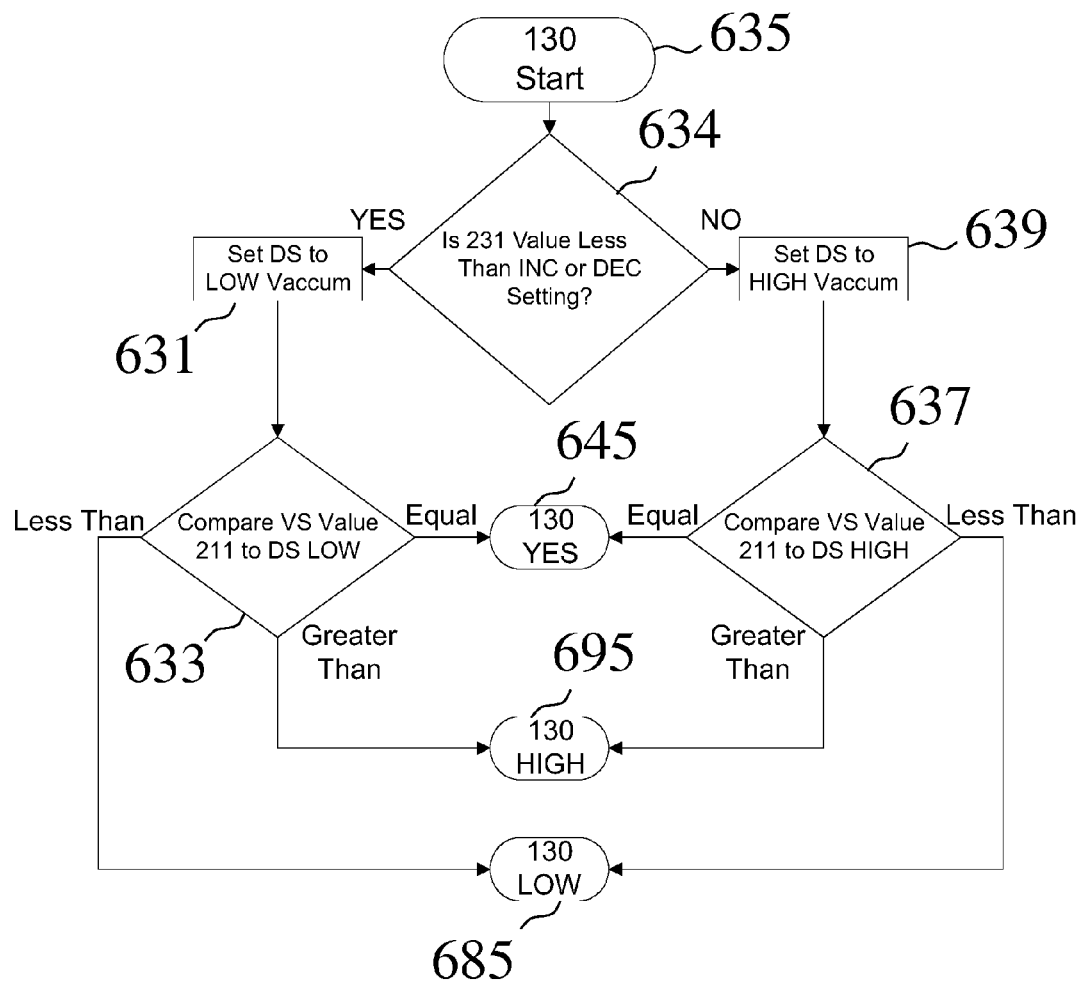
FIG. 6B is a flowchart showing the detail of decision block 130 for Tocodynamometer Contractions Tracking in accordance with an embodiment of the invention.
Figure 6C:
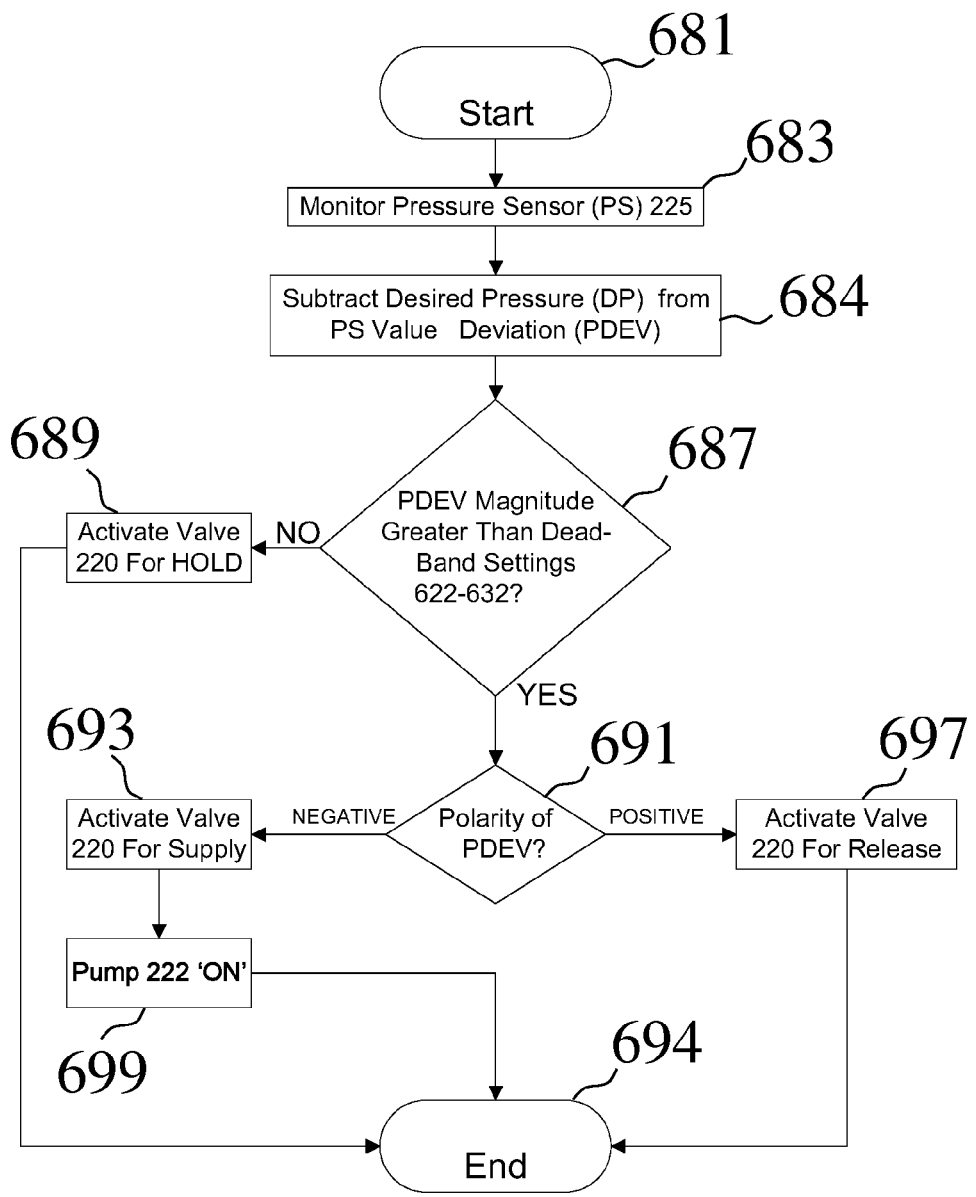
FIG. 6C is a flowchart showing the detail of decision block 132 when a combination cup is used in accordance with an embodiment of the invention.
Figure 7:
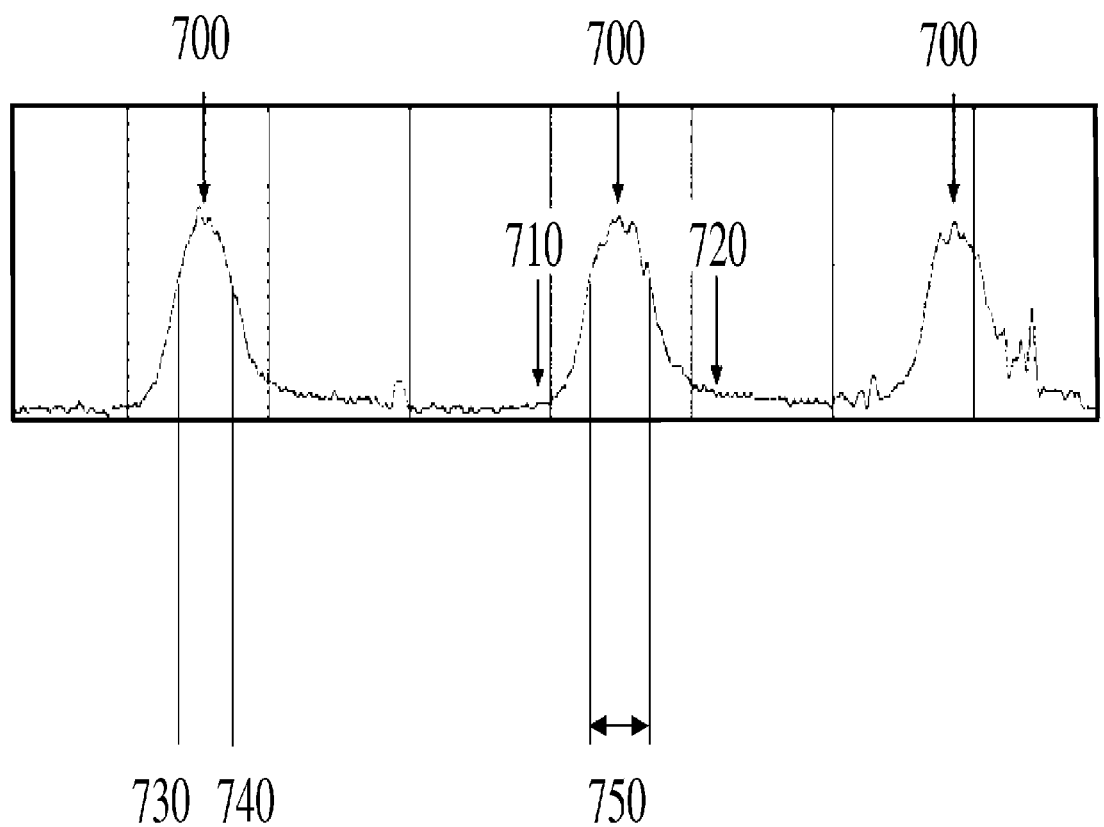
FIG. 7 is a plot of uterine pressure versus time illustrating how the length of time the fetal scalp is exposed to the maximum pressure can be minimized in accordance with an embodiment of the invention.

FIG. 7 shows a plot of uterine pressure versus time measured with either an external or intrauterine Tocodynamometer showing three peaks 700 each representing a separate contraction. In an embodiment of the present invention, the pumping device 301 utilizes uterine contraction data (from internal or external sources) to support proscribed vacuum safety limits as determined by the surgeon and/or attached device suppliers. With reference to FIG. 7, safety limits include: INC 730 the Pressure threshold setting used to trigger pumping device to attain Maximum value before Peak 700 (defined with Beginning at 710 with End at 720); Peak Period—measured time duration at Max vacuum 750; DEC 740 the Pressure threshold used to trigger release of vacuum pressure to attain and hold Minimum value at End 720 of contraction until next measurement. In an embodiment of the present invention, an aggregate of Peak Period 750 times can be used to determine a maximum time on vacuum to warn if a procedure has exceeded safe limits. In this manner, the time the maximum pressure is delivered to the fetal scalp or other body part can be reduced. This allows applying the suction device and sustaining the pressure for longer periods of time on a patient. In an embodiment of the present invention, the pumping device can also interpret contraction data to warn the surgeon of high Montevideo Units (MVU—the sum of the intensity of each contraction in a 10 minute period in mmHg) or of Tachysystole, Hypertonus, or Hyperstimulation conditions. Limits for fetal heart-rate can be set to affect the operation of the pumping device 301 to reduce or otherwise release any vacuum pressure if un-safe heart-rate(s) are encountered. The dwell time sets the wait time after the INC 730 threshold has been triggered to turn on the pump 214. After the pump 214 is turned on the vacuum continues to fall until the pump 214 has attained the desired pressure (see FIGS. 1 and 6). The dwell time also sets the wait time after the DEC 740 threshold has been triggered before the pump 214 is turned off. After the vacuum pump 214 is turned off, the pressure pump 224 turned on and the check valve 220 opened, the positive pressure is delivered and the vacuum fall until the desired pressure is attained (see FIGS. 1 and 6).

In an embodiment of the present invention, the vacuum pressure records can be stored in the processor memory during the execution of the medical procedure. In an embodiment of the present invention, upon the conclusion of the procedure, the vacuum pressure records, stored in the processor memory during the execution of the medical procedure can be retrieved. In an embodiment of the invention, the vacuum pressure records can be in the form of a histogram. The retrieval of the stored data can be performed by the simple insertion of a flash memory device into the external memory and interface port 201 or by connection of this port to a host computer for subsequent download. Once the medical procedure is completed, and/or the stored data is retrieved, the pumping device 301 can then be powered off using the power switch 202.

In an embodiment of the invention, the system control functionality of the pumping device 301 can be used to provide positive pressures, through the simple exchange of pump hose connectivity, sensor selection and processor firmware control algorithm changes. The device application can then be reversed, providing positive pressure, rather than vacuum, to devices requiring such positive pressure assistance.

In an embodiment of the invention, the system control functionality of the pumping device 301 can be used to provide positive pressure and negative vacuum simultaneously to a connected device via Positive Pressure Attachment Port 207 and Pressure Sensor 225). Utilizing control methods, algorithms, and procedure recording methods previously defined for vacuum only procedures; the device will operate as a dual port pump providing controlled positive and negative pressures.

In another embodiment of the invention, a Radio Frequency IDentification (RFID) tag is imbedded in one or more of: the pumping devices 435. In an embodiment of the invention, the RFID tag is used to identify the pumping device and thereby determine the parameters for operation of the pumping device 301. In one embodiment of the invention, the RFID tag operates using an Ultra High Frequency (UHF) signal. In another embodiment of the invention, the RFID tag operates using a microwave frequency signal.

In an embodiment of the present invention, a RFID reader is present in the pumping device 301 which can then read the RFID tags in the individual pumping devices. In an embodiment of the invention, the RFID reader can be positioned so that the RFID tag antenna is least affected by any conducting material.

In one embodiment the RFID tag is read only. In another embodiment, the RFID tag contains an Electrically Erasable Programmable Read-Only Memory (EPROM), which enables both read and write functions. In an embodiment of the invention, the RFID tag is passive. In another embodiment of the invention, the RFID tag is semi passive containing a source of energy such as a battery to allow the tag to be constantly powered. In a further embodiment of the invention, the RFID tag is active, containing an internal power source, such as a battery, which is used to power any Integrated Circuits (ICs) in the tag and generate the outgoing signal. In another embodiment, the tag has the ability to enable location sensing through a photo sensor.

In an embodiment of the invention, the pumping device 301 is able to monitor the type, previous use data and condition of the suction device 435. In this manner, a surgeon can choose when a surgical procedure warrants using the same pumping device 301 that has previously been used for a similar surgical procedure using similar parameters and under the same or similar conditions.

In one embodiment of the invention, means of communication with a base station is embedded in the pumping device 301. In one embodiment of the invention, the communication means utilizes one or more of a wireless local area network; a wireless wide area network; a cellular network; a satellite network; a Wi-Fi network; and a pager network. In one embodiment of the invention, a modem capable of communicating with one or more of the aforementioned networks is embedded in the pumping device 301. In the following discussion the term 'cellular modem' will be used to describe the device embedded. The term 'cellular modem' will be herein used to identify any device of comparable size capable of communicating over one or more of the aforementioned networks. In one embodiment of the invention, the cellular modem can be a Code Division Multiple Access (CDMA) modem. In an embodiment of the invention, a RFID reader and associate integrated circuit processor can be embedded together with the cellular modem in the pumping device 301. In such an embodiment, the RFID tags and RFID reader can be positioned to optimize the RFID read of the RFID tags from the available devices 435.

In an embodiment of the invention, a RFID reader and a cellular modem can be positioned in the pumping device 301; the RFID reader is in communication with one or more RFID readers, associated cellular modems and the RFID tags of one or more pumping devices 301. Through communications with the RFID reader and associated integrated circuit processor of the plurality of pumping devices 301, a RFID reader and associated integrated circuit processor is able to distinguish the RFID tag from pumping devices 301 in the vicinity based on one or more of location, strength of signal, variation of RFID tag signal with position, variation of RFID tag signal with time and prior input data. In an embodiment of the invention, one or more antenna inserted can be used to help discriminate the location of the pumping devices 301. In an embodiment of the invention, the RFID reader and associate processor can be in communication with the cellular modem. In an embodiment of the invention, the cellular modem is in communication with a base station and can transmit one or more parameters selected from the group consisting of one or more RFID tag location, one or more RFID tag identification code, pumping device 301, suction device 435, pumping device conditions, suction device conditions and time stamp.

In an embodiment of the invention, the pumping device 301 can be set to allow for a preset hysteresis. As shown in FIGS. 1 and 6(A), a preset vacuum (DS) 610 can be a user preference or set up based on the individual circumstances and sent to 130 Start (see 635). The pumping device 301 can calculate the Deviation (DEV) by subtracting DS 610 from VS (the measured vacuum at the Vacuum Sensor 211), see 655). The pumping device can interrogate whether the DEV magnitude is greater than the maximum acceptable vacuum 620 and the minimum acceptable vacuum 630 (Dead-Band Settings), see 660. Based on whether the DEV magnitude is greater than the Dead-Band Settings (620-630) the Dwell Timer can be stopped (see 690). The pumping device 301 can receive input from the user on whether Hysteresis or Dwell compensation is selected (see 665). This input can be a user preference or set up based on the individual circumstances. If Dwell compensation is selected, and the Dwell Timer is not active (see 670), then the Dwell Timer is started (see 690) and the pumping device 301 responds at 130 YES (see 645) (see FIG. 6(B)). In an embodiment of the invention, the pumping device 301 can be set to allow for a preset dwell time 750. If Dwell compensation is selected, and the Dwell Timer is active (see 670), then the pumping device 301 determines if the Preset Dwell Time 750 has been exceeded (see 675) and responds at 130 YES (see 645) (see FIG. 6(B)). If Hysteresis compensation is selected then the pumping device 301 determines the polarity of the DEV 680 and responds at 130 LOW (see 685) or 130 HIGH (see 695) (see FIG. 6(B)).

As shown in FIGS. 1 and 6(B), the pumping device 301 can track and respond to changes in the external signal 231 such as Tocodynamometer Contractions by comparing the external signal value with set values INC 730 or DEC 740 (see 634). In an embodiment of the invention, when the Tocodynamometer Contractions are less than INC 730, then the DS value is set to LOW Vacuum (see 631). When VS 211 is less than DS LOW (see 633) the pumping device 301 responds at 130 LOW (see 685). When VS 211 is greater than DS LOW (see 633) the pumping device 301 responds at 130 HIGH (see 695). When VS 211 is equal to DS LOW (see 633) the pumping device 301 responds at 130 YES (see 645). Alternatively, when the Tocodynamometer Contractions are not less than INC 730, then the DS value is set to HIGH Vacuum (see 639). When VS 211 is less than DS HIGH (see 637) the pumping device 301 responds at 130 LOW (see 685). When VS 211 is greater than DS HIGH (see 637) the pumping device 301 responds at 130 HIGH (see 695). When VS 211 is equal to DS HIGH (see 637) the pumping device 301 responds at 130 YES (see 645).

As shown in FIGS. 1 and 6(C), the pumping device 301 can monitor 683 and respond to changes in a pressure sensor (PS) 225 by comparing the PS value 225 with the desired pressure (DP) value to give the Pressure Deviation (PDEV) (see 684). The pumping device 301 can interrogate whether the PDEV magnitude is greater than the maximum acceptable pressure 622 and the minimum acceptable pressure 632 (Dead-Band Settings), see 687. Based on the PDEV magnitude not being greater than the Dead-Band Settings (622-632) the check valve 220 can be activated to hold (see 689) the algorithm ends (see 694) and the monitoring restarts. If the PDEV magnitude is greater than the Dead-Band Settings (622-632) then the pumping device 301 determines the polarity of the PDEV 691. If the polarity of PDEV is negative then the check valve 220 is activated (see 693) the pump 224 and pump head 222 are activated (see 699) the algorithm ends (see 694) and the monitoring restarts. If the polarity of PDEV is positive then the check valve 220 can be activated to release (see 697) the algorithm ends (see 694) and the monitoring restarts.

In an embodiment of the present invention, the RFID code uses the IEEE format and is Electronic Product Code (EPC) readable. In another embodiment of the invention the RFID code uses the UCC format and is Universal Product Code (UPC) readable. In another embodiment, the format is compatible for EPC, European Article Number (EAN) and UPC read and write functions.

In an embodiment of the invention, the device method or system can be used for the treatment of humans. In an embodiment of the invention, the device method or system can be used for the treatment of animals. In an embodiment of the invention, the device method or system can be used in veterinary applications. In an embodiment of the invention, the device method or system can be used in medical applications.

In an embodiment of the invention, a pumping device 301 and the suction device are assembled as an integral unit (see FIGS. 5A and B). As shown in FIG. 5A, the integral suction and pumping device 500 can have an accessible on off switch 202, located on or adjacent to the pumping device circuit board 209, which activates the pump control circuitry 210, wherein the vacuum sensor can monitor the vacuum applied to the suction device 435. These components can be attached within or onto integral suction and pumping device housing 510. The energy storage device 215 and the vacuum pump 214 can also be housed in the integral suction and pumping device housing 510, onto which the suction device can be attached 435. The integral suction and pumping device 500 can be a compact unit as shown in FIG. 5B. In an embodiment of the invention, an integral suction and pumping device 500 used for tamponade can be "joined" or can be assembled into one unit as shown in FIG. 5. In an embodiment of the invention, an integral suction and pumping device 500 is portable, ergonomic, and superior for in situ use. The integral suction and pumping device 500 can be utilized with a patient. As the patient moves, the device can move to compensate for the movement. In contrast, if the pumping device was separate, or relied upon a tether to hold the device to the patient, then movement could jar and detach the suction device. In an embodiment of the invention, in an integral suction and pumping device 500, the suction device is integrated into the pumping device for use by a first-responder to treat a wound. In an embodiment of the invention, in an integral suction and pumping device 500, the suction device is integrated into the pumping device for use by a first-responder to curtail bleeding. In an embodiment of the invention, an integral suction and pumping device 500 can be used in a battlefield or any similar trauma inducing setting to stem bleeding from laceration sites. In an embodiment of the invention, an integral suction and pumping device 500 can be used in a battlefield to treat one or more wound sites. In an embodiment of the invention, a sterilized material is used to clean the wound prior to applying the integral suction and pumping device 500 which can be positioned with the suction device 435 fully encompassing multiple wound sites. In an embodiment of the invention, a sterilized material is used to temporarily remove blood from the laceration sites in order to identify the site(s) of bleeding, so that the integral suction and pumping device 500 can be positioned with the suction device 435 fully encompassing the multiple laceration sites. In an embodiment of the invention, the integral suction and pumping device 500 can be packaged in a sterilized container so that the wound is not contaminated when the integral suction and pumping device 500 is applied to the mammal. This will help ensure that the wound site(s) can be kept clean and free of bacteria. In an embodiment of the invention, the integral suction and pumping device 500 can be packaged in a sterilized container so that the laceration sites are not contaminated when the integral suction and pumping device 500 is applied to the mammal. This will help ensure that the laceration site(s) can be kept clean and free of bacteria. In an embodiment of the invention, the integral suction and pumping device 500 can be sealed in a hermetically sealed package which is opened directly prior to the integral suction and pumping device 500 being applied to the mammal. In an embodiment of the invention, once the wound or laceration site can be established an integral suction and pumping device 500 can be applied to treat the mammal. In an embodiment of the invention, an integral suction and pumping device 500 can be used once and then discarded to minimize the risk of contamination. In an embodiment of the invention, an integral suction and pumping device 500 can be used once and then discarded to eliminate the risk of blood or tissue contamination. In an embodiment of the invention, the integral suction and pumping device 500 can replace traditional dressings and/or a tourniquet.

In an embodiment of the invention, unlike a traditional tourniquet, the vacuum cup could be applied to external skin on a body part that is the vacuum cup is not limited to use on a limb. Alternatively, it can be applied to any smooth surface on an internal body structure or organ. In an embodiment of the invention, a pumping device to enable a specified vacuum to be applied to a suction device attached to tissue, comprises a sensor for monitoring a vacuum applied to the suction device, a pump for increasing the vacuum to the suction device, a valve for immediately releasing the vacuum applied to the suction device to release the tissue and a control circuit. Wherein the control circuit controls two or more functions selected from the group consisting of activating the pump, opening the valve and adjusting operating parameters of the pumping device. Wherein activating the pump applies the specified positive or negative pressure to the suction device. Wherein opening the valve immediately releases the specified positive or negative pressure applied to the suction device. Wherein adjusting operating parameters of the pumping device modifies the specified positive or negative pressure. Wherein the control circuit is operated while holding the suction device.

In an embodiment of the invention, the pressure device further comprises a control unit mounted one or both on and adjacent to the suction device, wherein the control unit allows one or more of control of the specified positive or negative pressure applied to the suction device, control of the pumping device and adjustment of the specified positive or negative pressure device settings during the procedure.

In an embodiment of the invention, the pumping device further comprises a foot switch, wherein the foot switch allows one or more of control of the specified positive or negative pressure applied to the suction device, control of the pumping device and adjustment of the pumping device settings during the procedure.

In an embodiment of the invention, the pumping device further comprises one or both visual and audio feedback that allows one or more methods of control of the specified positive or negative pressure applied to the suction device, control of the pumping device and adjustment of the pumping device settings during the procedure.

In an embodiment of the invention, the pumping device is portable. In an embodiment of the invention, the pumping device is hand held. In an embodiment of the invention, the pumping device is portable and hand held.

In an embodiment of the invention, a method of adjusting and monitoring a pumping device during a surgical procedure, comprises receiving the suction device attached to tissue and receiving a pumping device for applying a specified positive or negative pressure to the suction device during the surgical procedure, wherein the pumping device one or both receives and has preset parameters to control the specified positive or negative pressure to be applied to the suction device. Activating the pumping device, wherein the pumping device functions include monitoring the specified positive or negative pressure applied to the suction device via a sensor, comparing the specified positive or negative pressure applied to the suction device and the parameters at regular time intervals using a processor and automatically increasing the specified positive or negative pressure to the suction device when the comparison indicates an increased specified positive or negative pressure is required. The method further comprises monitoring the pumping device during the surgical procedure using one or both audio or visual feedback from the pumping device and adjusting the parameters selected in response to changed conditions of the surgical procedure while the specified positive or negative pressure is applied to the tissue. In an embodiment of the invention, the specified positive or negative pressure is adjusted to control against separation of the suction device from the tissue at the rim of the suction device where it contacts the tissue.

In an embodiment of the invention, a system for adjusting and monitoring a suction device comprises a pumping device for applying a specified positive or negative pressure to the suction device, wherein the pumping device includes an RFID tag reader, wherein the RFID tag reader can read an RFID tag on the suction device, an input module for selecting parameters for use with the pumping device, wherein the input module selects parameters based at least in part on the suction device selected, a sensor for monitoring the specified positive or negative pressure applied by the pumping device to the suction device and a processor for comparing the specified positive or negative pressure applied to the suction device and the selected parameters and automatically activating the pumping device to increase the specified positive or negative pressure to the suction device when the comparison indicates an increased specified positive or negative pressure is required, the suction device including the RFID tag and a control unit, wherein the RFID tag identifies parameters associated with the suction device, wherein the control unit adjusts the pumping device parameters in response to changed conditions and audio or visual feedback of the specified positive or negative pressure applied to the suction device during the surgical procedure, wherein based on audio or visual feedback the control unit is used to adjust the specified positive or negative pressure device parameters.

In an embodiment of the invention, a system for a first responder to minimize bleeding of a wound in a mammal comprises an integral suction and pumping device for applying a specified positive or negative pressure to the wound. The integral suction and pumping device includes a switch to activate the integral suction and pumping device, a suction cup, a relief valve, a vacuum pump, wherein the vacuum pump generates a vacuum at the suction cup, a sensor for monitoring the vacuum at the suction cup and a processor. The processor compares the vacuum applied to the suction cup and selected parameters and automatically activating the vacuum pump to increase the vacuum to the suction cup when the comparison indicates an increased vacuum is required and one or both deactivating the vacuum pump and automatically opening the relief valve when the comparison indicates a decreased specified positive or negative pressure is required. Application of the suction cup and the vacuum to the wound attaches the integral suction and pumping device to the mammal such that movement of the mammal does not detach the integral suction and pumping device. The system further comprises a material to one or both identify the wound and wipe blood away from the wound. After the wound site(s) are identified the integral suction and pumping device is applied to the wound and activated to one or more of treat the wound, stop or minimize bleeding of a wound.

In an embodiment of the invention, a system for adjusting and monitoring a suction device during a surgical procedure comprises a pumping device for applying a specified positive or negative pressure to the suction device. The pumping device includes an input module for selecting parameters for use with the pumping device, wherein the input module selects parameters based at least in part on the suction device selected, a sensor for monitoring the specified positive or negative pressure applied by the pumping device to the suction device, a processor for comparing the specified positive or negative pressure applied to the suction device and the selected parameters and automatically activating the pumping device to increase the positive or negative pressure to the suction device when the comparison indicates an increased specified positive or negative pressure is required and audio or visual feedback to monitor the specified positive or negative pressure applied to the suction device during the surgical procedure. The system also comprises the suction device attached to a subject's tissue and a device to monitor the subject's pulse, wherein the subject's pulse is used to adjust the pumping device parameters.

In an embodiment of the invention the pumping device 301 can be applied in any scientific, manufacturing, or industrial apparatus that requires the use of a regulated constant or variable vacuum. This can include laboratory equipment that requires vacuum assisted grasping, reactions, sampling, storage or any other clinical procedure. The manipulation of components, fluids or assemblies used in a manufacturing process, including: precision handling, clean-room transport, and material transport can also be supported.

In an embodiment of the present invention, a method of assisting a surgeon in an operation comprises receiving a pumping device adapted for applying a vacuum to a suction device, where the pumping device one or both receives and has preset parameters to control the vacuum to be applied to a tissue of a patient during the operation, receiving the suction device and attaching the suction device to the tissue, receiving one or more sensors including a vacuum sensor for monitoring the operation, positioning the one or more sensors for monitoring the operation, begin monitoring the data from the one or more sensors, and activating the pumping device, where the pumping device functions include: monitoring the vacuum applied to the tissue via the vacuum sensor, comparing the data from the one or more sensors and the preset parameters using an algorithm processed on a processor, automatically increasing the vacuum applied to the tissue when the comparison indicates a greater vacuum is required to assist the operation, and automatically decreasing the vacuum applied to the tissue when the comparison indicates a reduced vacuum is required to assist the operation.

In an embodiment of the present invention, a device to adjust a vacuum applied to a tissue of a patient comprises a suction device, where the suction device is adapted to be attached to a tissue, one or more sensors for monitoring the patient including a vacuum sensor for monitoring a vacuum applied to the tissue of the patient, a pump for supplying both positive pressure and negative pressure to adjust the vacuum applied to the tissue, and a processor for adjusting the vacuum applied to the tissue where the processor activates the pump to perform functions including: applying negative pressure to the tissue when the one or more sensors monitoring the patient indicate an increase in vacuum is required, applying positive pressure to the tissue to reduce the vacuum when the one or more sensors monitoring the patient indicate a decrease in vacuum is required, and applying positive pressure to release the suction device.

In an embodiment of the present invention, a device to adjust a vacuum applied to a tissue of a patient comprises a suction device, where the suction device is adapted to be attached to a tissue, one or more sensors for monitoring the patient including a vacuum sensor for monitoring a vacuum applied to the tissue of the patient, a pump for supplying both positive pressure and negative pressure to adjust the vacuum applied to the tissue, and a processor for adjusting the vacuum applied to the tissue where the processor activates the pump to perform functions including: applying negative pressure to the tissue when the one or more sensors monitoring the patient indicate an increase in vacuum is required, applying positive pressure to the tissue to reduce the vacuum when the one or more sensors monitoring the patient indicate a decrease in vacuum is required, and applying positive pressure to one or both release the suction device and pressurize an independent chamber within the suction device.

In an embodiment of the present invention, a device to adjust a vacuum applied to a tissue of a patient comprises a suction device, where the suction device is adapted to be attached to a tissue, a vacuum sensor for monitoring a vacuum applied to the tissue of the patient, one or more sensors for monitoring the patient, a pump for supplying both positive pressure and negative pressure to adjust the vacuum applied to the tissue, and a processor for adjusting the vacuum applied to the tissue where the processor activates the pump to perform functions including applying negative pressure to the tissue when the one or more sensors monitoring the patient indicate an increase in vacuum is required, applying positive pressure to the tissue to reduce the vacuum when the one or more sensors monitoring the patient indicate a decrease in vacuum is required, and applying positive pressure to release the suction device.

In an embodiment of the present invention, a device to adjust a vacuum applied to a tissue of a patient, comprises a suction device, where the suction device is adapted to be attached to a tissue, a vacuum sensor for monitoring a vacuum applied to the tissue of the patient, one or more sensors for monitoring the patient, a pump for simultaneously supplying both positive pressure and negative pressure to adjust the vacuum applied to the tissue, and a processor for adjusting the vacuum applied to the tissue where the processor activates the pump to perform functions including applying positive pressure and negative pressure simultaneously to the suction device, where the negative pressure exceeds the positive pressure to increase the vacuum applied to the tissue in a controlled manner, when the one or more sensors monitoring the patient indicate an increase in vacuum is required and applying positive pressure and negative pressure simultaneously to the suction device, where the positive pressure exceeds the negative pressure to reduce the vacuum applied to the tissue in a controlled manner, when one or both the one or more sensors monitoring the patient indicate a decrease in vacuum is required and the operation is completed.

In an embodiment of the present invention, a method of stabilizing a wound on a mammal comprises receiving a pumping device adapted for applying a vacuum to a suction device, where the pumping device one or both receives and has preset parameters to control the vacuum to be applied to the wound, receiving the suction device including a vacuum sensor and attaching the suction device to the wound, receiving one or more sensors for monitoring one or both the wound and the mammal, positioning the one or more sensors for monitoring one or both the condition of the wound and the condition of the mammal, begin monitoring the data from the one or more sensors, activate the pumping device, where the pumping device functions include monitoring the vacuum applied to the tissue via the vacuum sensor, comparing the vacuum applied to the tissue, the data from the one or more sensors and the preset parameters using an algorithm processed on a processor, automatically applying a combination of positive pressure and negative pressure to the tissue, where the negative pressure exceeds the positive pressure to increase the vacuum applied to the tissue when the comparison indicates a greater vacuum is required to assist the operation and automatically applying a combination of positive pressure and negative pressure to the tissue, where the positive pressure exceeds the negative pressure to decrease the vacuum applied to the tissue when the comparison indicates a reduced vacuum is required to assist the operation.

In an embodiment of the present invention, a device to adjust a vacuum applied to a tissue of a patient comprises a suction device with a plurality of compartments, where the suction device is adapted to be attached to the tissue of the patient through at least one of the plurality of compartments, where the suction device is adapted to deliver an agent to the tissue of the patient through at least one of the plurality of compartments, a vacuum sensor for monitoring a vacuum applied to the tissue of the patient, one or more sensors for monitoring the patient, a pump for simultaneously supplying both positive pressure and negative pressure to one or more of the plurality of compartments and a processor for adjusting the vacuum applied to the tissue where the processor activates the pump to perform functions including applying one or both positive pressure and negative pressure to the at least one of the plurality of compartments attaching the suction device to the tissue of the patient when the one or more sensors monitoring the patient indicate an increase or decrease in vacuum is required and applying one or both positive pressure and negative pressure to the at least one of the plurality of compartments delivering the agent to the tissue of the patient when the one or more sensors monitoring the patient indicate an increase or decrease in the agent is required.

In an embodiment of the present invention, a device to adjust a vacuum applied to a tissue of a patient comprises a suction device with a plurality of compartments, where the suction device is adapted to be attached to the tissue of the patient through at least one of the plurality of compartments, where the suction device is adapted to deliver an agent to the tissue of the patient through at least one of the plurality of compartments, a vacuum sensor for monitoring a vacuum applied to the tissue of the patient, one or more sensors for monitoring one or more parameters selected from the group consisting of compression of a wound, analgesia of the patient, heart-rate of a fetus, heart rate of the patient, blood pressure of the fetus and blood pressure of the patient, a pump for simultaneously supplying both positive pressure and negative pressure to one or more of the plurality of compartments and a processor for adjusting the vacuum applied to the tissue where the processor activates the pump to perform functions including applying one or both positive pressure and negative pressure to the at least one of the plurality of compartments attaching the suction device to the tissue of the patient when the one or more sensors monitoring the patient indicate an increase or decrease in vacuum is required and applying one or both positive pressure and negative pressure to the at least one of the plurality of compartments delivering the agent to the tissue of the patient when the one or more sensors monitoring the patient indicate an increase or decrease in the agent is required.

In an embodiment of the present invention, a device to adjust a vacuum applied to a tissue of a patient comprises a suction device with a plurality of compartments, where the suction device is adapted to be attached to the tissue of the patient through at least one of the plurality of compartments, where the suction device is adapted to deliver an agent to the tissue of the patient through at least one of the plurality of compartments, a vacuum sensor for monitoring a vacuum applied to the tissue of the patient, one or more sensors for monitoring the patient, a pump for simultaneously supplying both positive pressure and negative pressure to one or more of the plurality of compartments, where a positive pressure inlet to the suction device and a negative pressure inlet to the suction device are positioned to adjust the decrease in vacuum in the suction device in a controlled manner and a processor for adjusting the vacuum applied to the tissue where the processor activates the pump to perform functions including applying one or both positive pressure and negative pressure to the at least one of the plurality of compartments attaching the suction device to the tissue of the patient when the one or more sensors monitoring the patient indicate an increase or decrease in vacuum is required and applying one or both positive pressure and negative pressure to the at least one of the plurality of compartments delivering the agent to the tissue of the patient when the one or more sensors monitoring the patient indicate an increase or decrease in the agent is required.

In an embodiment of the present invention, a device to adjust a vacuum applied to a tissue of a patient comprises a suction device with a plurality of compartments, where the suction device is adapted to be attached to the tissue of the patient through at least one of the plurality of compartments, where the suction device is adapted to deliver an agent to the tissue of the patient through at least one of the plurality of compartments, a vacuum sensor for monitoring a vacuum applied to the tissue of the patient, one or more sensors for monitoring the patient, a pump for simultaneously supplying both positive pressure and negative pressure to one or more of the plurality of compartments, where a positive pressure inlet to the suction device and a negative pressure inlet to the suction device are positioned to adjust the increase in vacuum in the suction device in a controlled manner and a processor for adjusting the vacuum applied to the tissue where the processor activates the pump to perform functions including applying one or both positive pressure and negative pressure to the at least one of the plurality of compartments attaching the suction device to the tissue of the patient when the one or more sensors monitoring the patient indicate an increase or decrease in vacuum is required and applying one or both positive pressure and negative pressure to the at least one of the plurality of compartments delivering the agent to the tissue of the patient when the one or more sensors monitoring the patient indicate an increase or decrease in the agent is required.

In an embodiment of the present invention, a device to adjust a vacuum applied to a tissue of a patient comprises a suction device with an attachment compartment and an administration compartment, where the suction device is adapted to be attached to the tissue of the patient through the attachment chamber which includes a negative pressure inlet, where the suction device is adapted to deliver an agent to the tissue of the patient through the administration compartment which includes a positive pressure inlet, where the attachment compartment and the administration compartment are independent and exclusive compartments within the suction device, a vacuum sensor for monitoring a vacuum applied to the tissue of the patient, one or more sensors for monitoring the patient, a pump for simultaneously supplying both positive and negative pressure to one or both of the attachment compartment and the administration compartment, where the positive pressure inlet and the negative pressure inlet are positioned to provide simultaneous vacuum pressure and positive pressure and a processor for adjusting the vacuum applied to the tissue where the processor activates the pump to perform functions including applying one or both positive pressure and negative pressure to the at least one of the plurality of compartments attaching the suction device to the tissue of the patient when the one or more sensors monitoring the patient indicate an increase or decrease in vacuum is required and applying one or both positive pressure and negative pressure to the at least one of the plurality of compartments delivering the agent to the tissue of the patient when the one or more sensors monitoring the patient indicate an increase or decrease in the agent is required.

In an embodiment of the present invention, a device to adjust a vacuum applied to a tissue of a patient comprises a suction device with a plurality of compartments, where the suction device is adapted to be attached to the tissue of the patient through at least one of the plurality of compartments, where the suction device is adapted to deliver an agent to the tissue of the patient through at least one of the plurality of compartments, a vacuum sensor for monitoring a vacuum applied to the tissue of the patient, one or more sensors for monitoring the patient, a pump for simultaneously supplying both positive pressure and negative pressure to one or more of the plurality of compartments and a processor for adjusting the vacuum applied to the tissue where the processor activates the pump to perform functions including applying positive pressure in excess of the negative pressure applied in order to reduce the vacuum applied to the tissue in a controlled manner based on visual inspection of wound surfaces visually for apposition.

In an embodiment of the present invention, a method of stabilizing a wound on a mammal comprises receiving a pumping device adapted for applying a vacuum to a suction device, where the pumping device one or both receives and has preset parameters to control the vacuum to be applied to the wound, receiving the suction device including a compartment for delivering an agent and a vacuum sensor, attaching the suction device to the wound, receiving one or more sensors for monitoring one or both the wound and the mammal, a control sensor under manual control of the patient to adjust the vacuum being delivered, positioning the one or more sensors for monitoring one or both the condition of the wound and the condition of the mammal, beginning monitoring of the data from the one or more sensors, activating the pumping device, where the pumping device functions include monitoring the vacuum applied to the tissue via the vacuum sensor, comparing the vacuum applied to the tissue, the data from the one or more sensors and the preset parameters using an algorithm processed on a processor, automatically applying positive pressure in excess of the negative pressure applied in order to reduce the vacuum applied to the wound in a controlled manner based on visual inspection of wound surfaces visually for apposition.

In an embodiment of the present invention, a method of assisting a surgeon in an operation comprises receiving a pumping device adapted for applying a vacuum to a suction device, where the pumping device one or both receives and has preset parameters to control the vacuum to be applied to a tissue surface of a patient during the operation, receiving the suction device including a vacuum sensor and attaching the suction device to the tissue surface, receiving one or more sensors for monitoring the operation, where one of the one or more sensors is a compression sensor adapted to measure compression of a wound in a tissue site on or adjacent to the tissue surface, positioning one or more sensors for monitoring the operation, beginning monitoring of data from the one or more sensors and activating the pumping device, where the pumping device functions include monitoring the vacuum applied to the tissue surface via the vacuum sensor, comparing the data from the one or more sensors and the preset parameters using an algorithm processed on a processor, automatically applying a combination of a positive pressure and a negative pressure to the tissue surface, where the negative pressure exceeds the positive pressure to increase the vacuum applied to the tissue surface when comparing the data indicates a greater vacuum is required to assist the operation and automatically applying a combination of positive pressure and negative pressure to the tissue surface, where the positive pressure exceeds the negative pressure to decrease the vacuum applied to the tissue surface when comparing the data indicates a reduced vacuum is required to assist the operation.

In an embodiment of the present invention, a device to adjust a vacuum applied to a tissue of a patient comprises a suction device with a plurality of compartments, where the suction device is adapted to be attached to the tissue of the patient through at least one of the plurality of compartments, where the suction device is adapted to deliver an agent to the tissue of the patient through at least one of the plurality of compartments, a vacuum sensor for monitoring a vacuum applied to the tissue of the patient, one or more sensors for monitoring the patient, where one of the one or more sensors is a compression sensor adapted to measure compression of a wound in a tissue site on or adjacent to the tissue surface, a pump for simultaneously supplying both positive pressure and negative pressure to one or more of the plurality of compartments and a processor for adjusting the vacuum applied to the tissue where the processor activates the pump to perform functions including applying one or both positive pressure and negative pressure to the at least one of the plurality of compartments attaching the suction device to the tissue of the patient when the one or more sensors monitoring the patient indicate an increase or decrease in vacuum is required and applying one or both positive pressure and negative pressure to the at least one of the plurality of compartments delivering the agent to the tissue of the patient when the one or more sensors monitoring the patient indicate an increase or decrease in the agent is required.

In an embodiment of the present invention, a method of stabilizing a wound on a mammal comprises receiving a pumping device adapted for applying a vacuum to a suction device, where the pumping device one or both receives and has preset parameters to control the vacuum to be applied to the wound, receiving the suction device including a compartment for delivering an agent and a vacuum sensor, attaching the suction device to the wound, receiving one or more sensors for monitoring one or more of a condition of the wound, where one of the one or more sensors is a compression sensor adapted to measure compression of the wound in a site on or adjacent to the wound, a condition of the mammal and the mammal, positioning the one or more sensors for monitoring one or both the condition of the wound and the condition of the mammal, beginning monitoring of the data from the one or more sensors, activating the pumping device, where the pumping device functions include monitoring the vacuum applied to the wound via the vacuum sensor, comparing the vacuum applied to the wound, the data from the one or more sensors and the preset parameters using an algorithm processed on a processor, automatically applying one or both positive pressure and negative pressure to the wound when the one or more sensors monitoring the mammal indicate an increase or decrease in vacuum is required and automatically applying one or both positive pressure and negative pressure to the compartment for delivering the agent when the one or more sensors monitoring the mammal indicate an increase or decrease in the agent is required.

In an embodiment of the present invention, a device to adjust a vacuum applied to a tissue of a patient comprises a suction device with a plurality of compartments, where the suction device is adapted to be attached to the tissue of the patient through at least one of the plurality of compartments, where the suction device is adapted to deliver an agent to the tissue of the patient through at least one of the plurality of compartments, a vacuum sensor for monitoring a vacuum applied to the tissue of the patient, one or more sensors for monitoring the patient, a control sensor under manual control of the patient to adjust the dose of the agent being delivered, a pump for simultaneously supplying both positive pressure and negative pressure to one or more of the plurality of compartments and a processor for adjusting the vacuum applied to the tissue where the processor activates the pump to perform functions including applying one or both positive pressure and negative pressure to the at least one of the plurality of compartments attaching the suction device to the tissue of the patient when the one or more sensors monitoring the patient indicate an increase or decrease in vacuum is required and applying one or both positive pressure and negative pressure to the at least one of the plurality of compartments delivering the agent to the tissue of the patient when the one or more sensors monitoring the patient indicate an increase or decrease in the agent is required.

In an embodiment of the present invention, a method of assisting a surgeon in an operation comprises receiving a pumping device adapted for applying a vacuum to a suction device, where the pumping device one or both receives and has preset parameters to control the vacuum to be applied to a tissue surface of a patient during the operation, receiving the suction device including a vacuum sensor and attaching the suction device to the tissue surface, receiving one or more sensors for monitoring the operation, where one of the one or more sensors is a compression sensor adapted to measure compression of a wound in a tissue site on or adjacent to the tissue surface, where one of the one or more sensors is a control sensor under manual control of the patient to adjust the vacuum being delivered, positioning one or more sensors for monitoring the operation, beginning monitoring of data from the one or more sensors and activating the pumping device, where the pumping device functions include monitoring the vacuum applied to the tissue surface via the vacuum sensor, comparing the data from the one or more sensors and the preset parameters using an algorithm processed on a processor, automatically applying a combination of a positive pressure and a negative pressure to the tissue surface, where the negative pressure exceeds the positive pressure to increase the vacuum applied to the tissue surface when comparing the data indicates a greater vacuum is required to assist the operation and automatically applying a combination of positive pressure and negative pressure to the tissue surface, where the positive pressure exceeds the negative pressure to decrease the vacuum applied to the tissue surface when comparing the data indicates a reduced vacuum is required to assist the operation Various embodiments can be implemented using a conventional general purpose or specialized digital computer(s) and/or processor(s) programmed according to the teachings of the present disclosure, as will be apparent to those skilled in the computer art. Appropriate software coding can readily be prepared by skilled programmers based on the teachings of the present disclosure, as will be apparent to those skilled in the software art. The invention can also be implemented by the preparation of integrated circuits and/or by interconnecting an appropriate network of component circuits, as will be readily apparent to those skilled in the art.

Embodiments of the present invention can include a computer readable medium, such as computer readable storage medium. The computer readable storage medium can have stored instructions which can be used to program a computer to perform any of the features present herein. The storage medium can include, but is not limited to, any type of disk including floppy disks, optical discs, DVD, CD-ROMs, micro drive, and magneto-optical disks, ROMs, RAMs, EPROMs, EEPROMs, DRAMs, flash memory or any media or device suitable for storing instructions and/or data. The present invention can include software for controlling both the hardware of a computer, such as general purpose/specialized computer(s) or microprocessor(s), and for enabling them to interact with a human user or other mechanism utilizing the results of the present invention. Such software can include, but is not limited to, device drivers, operating systems, execution environments/containers, and user applications.

Embodiments of the present invention can include providing code for implementing processes of the present invention. The providing can include providing code to a user in any manner. For example, the providing can include transmitting digital signals containing the code to a user, providing the code on a physical media to a user, or any other method of making the code available.

Embodiments of the present invention can include a computer-implemented method for transmitting the code which can be executed at a computer to perform any of the processes of embodiments of the present invention. The transmitting can include transfer through any portion of a network, such as the Internet; through wires, the atmosphere or space; or any other type of transmission. The transmitting can include initiating a transmission of code; or causing the code to pass into any region or country from another region or country. A transmission to a user can include any transmission received by the user in any region or country, regardless of the location from which the transmission is sent.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

What is claimed is:

1. A method of assisting a surgeon in an operation, comprising:
    receiving a pumping device adapted for applying a vacuum to a suction device;
    receiving the suction device including a vacuum sensor; and
    activating the pumping device to attach the suction device to a tissue surface via application of a vacuum, where the vacuum between the suction device and the tissue surface forms a tamponade to minimize fluid flow at the tissue surface, where the pumping device functions include:
        reading the vacuum sensor;
        monitoring a patient physiological parameter and a fetus physiological parameter;
        applying a combination of a positive pressure and a negative pressure to the tissue surface; and
        automatically applying one or both positive pressure and negative pressure to the tissue surface;
        based on the vacuum sensor reading, controlling the pumping device to either increase, maintain, decrease or not pump to one or both attain and maintain a vacuum condition; and
        controlling the vacuum condition based on the patient physiological parameter and the fetus physiological parameter.

2. The method of claim 1, further comprising a valve to reduce negative pressure through atmospheric venting.

3. The method of claim 1, where the negative pressure maintains attachment to the tissue surface.

4. The method of claim 1, where the positive pressure applies targeted surface compression to the tissue surface.

5. The method of claim 1, where the pumping device is integral to the suction device.

6. The method of claim 1, where the patient physiological parameter is selected from the group consisting of fetal pulse, patient pulse, fetal heart rate, patient heart rate, fetal blood pressure, patient blood pressure, position of the fetus, condition of the fetus, condition of the patient, compression of fetal tissue surface, compression of patient tissue surface, uterine contraction occurrence, uterine contraction pressure and tocodynamometer contractions.

7. The method of claim 1, where the tissue surface is a scalp of a fetus.

8. The method of claim 1, where an aggregate of peak intensity of the data from monitoring the patient physiological parameter over a time period is used to one or both warn of a safety issue and release vacuum pressure.

9. The method of claim 1, where the positive pressure exceeds the negative pressure applied in order to reduce the vacuum applied to the tissue surface in a controlled manner when a Tocodynamometer Contractions Tracking sensor indicates uterus at rest.

10. The method of claim 1, where the positive pressure exceeds the negative pressure applied in order to reduce the vacuum applied to the tissue surface in a controlled manner when a systemic blood pressure sensor indicates diastole.

11. The method of claim 1, where the negative pressure exceeds the positive pressure applied in order to increase the vacuum applied to the tissue surface in a controlled manner.

12. The method of claim 1, where the positive pressure exceeds the negative pressure applied in order to reduce the vacuum applied to the tissue surface in a controlled manner.

13. The method of claim 12, where the positive pressure supplied by the pumping device is used to immediately release the vacuum to detach the suction device from the tissue surface.

14. The method of claim 12, where the negative pressure supplied by the pumping device is used to control a rate of detachment of the suction device from the tissue surface.

15. The method of claim 1, where the patient physiological parameter is a heart rate sensor adapted to measure a heart rate of the patient.

16. The method of claim 15, where the vacuum applied to the tissue surface is decreased when the heart rate sensor indicates a decreased heart rate is required.

17. The method of claim 15, where the pumping device one or both reduces and releases the vacuum based on the heart rate monitoring.

18. A device to adjust a vacuum applied to a tissue of a patient, comprising:
    a suction device with a plurality of compartments, where the suction device is adapted to be attached to the tissue of the patient through at least one of the plurality of compartments, where the suction device is adapted to deliver an agent to the tissue of the patient through at least one of the plurality of compartments;

a vacuum sensor for monitoring a vacuum applied to the tissue of the patient;

one or more sensors for monitoring the patient;

a pump for simultaneously supplying both positive pressure and negative pressure to one or more of the plurality of compartments; and a processor for adjusting the vacuum applied to the tissue where the processor activates the pump to perform functions including:

applying one or both positive pressure and negative pressure to the at least one of the plurality of compartments attaching the suction device to the tissue of the patient, where the vacuum between the suction device and the tissue of the patient forms a tamponade stopping fluid flow at the tissue of the patient to one or both attain and maintain a vacuum condition; and applying one or both positive pressure and negative pressure to the at least one of the plurality of compartments delivering the agent to the tissue of the patient when the one or more sensors monitoring the patient indicate an increase or decrease in the agent is required.

19. A method of stabilizing a wound on a mammal, comprising:

receiving a pumping device adapted for applying a vacuum to a suction device, where the pumping device one or both receives and has preset parameters to control the vacuum to be applied to the wound;

receiving the suction device adapted to enclose the wound, including a compartment for delivering an agent and a vacuum sensor;

locating the suction device around the wound;

receiving one or more sensors for monitoring a mammal physiological parameter selected from the group consisting of a condition of the wound, the wound, a condition of the mammal and the mammal;

positioning the one or more sensors for monitoring one or both the condition of the wound and the condition of the mammal;

beginning monitoring of the data from the one or more sensors;

activating the pumping device to secure the suction device to the wound via application of a vacuum, where the vacuum between the suction device and the wound forms a tamponade restricting fluid flow at the wound, where the pumping device functions include:

monitoring the vacuum applied to the wound via the vacuum sensor;

comparing the vacuum applied to the wound, the data from the one or more sensors and the preset parameters using an algorithm processed on a processor;

automatically applying one or both positive pressure and negative pressure to the wound to one or both attain and maintain a vacuum condition as indicated by the vacuum sensor; and automatically controlling the vacuum above or below the vacuum condition based on the mammal physiological parameter.

20. A method of assisting a surgeon during delivery of a fetus, comprising:

receiving a pumping device adapted for applying a vacuum to a suction device;

receiving the suction device including a vacuum sensor; and activating the pumping device to attach the suction device to the fetal scalp via application of a vacuum, where the vacuum between the suction device and the fetal scalp forms a tamponade to stop flow and eliminate vacuum leakage at the fetal scalp, where the pumping device functions include:

reading the vacuum sensor;

monitoring a patient physiological parameter selected from the group consisting of fetal pulse, patient pulse, fetal heart rate, patient heart rate, fetal blood pressure, patient blood pressure, position of the fetus, condition of the fetus, condition of the patient, compression of fetal tissue surface, compression of patient tissue surface, uterine contraction occurrence, uterine contraction pressure and tocodynamometer contractions;

applying via the pumping device a combination of a positive pressure and a negative pressure to the fetal scalp to one or both attain and maintain a vacuum condition as indicated by the vacuum sensor reading; and controlling the vacuum above or below the vacuum condition based on the patient physiological parameter.

* * * * *